United States Patent
Kim et al.

(10) Patent No.: US 10,322,135 B2
(45) Date of Patent: Jun. 18, 2019

(54) PHARMACEUTICAL COMPOSITION COMPRISING INDOLE COMPOUND

(71) Applicant: LG CHEM, LTD., Seoul (KR)

(72) Inventors: Soon Ha Kim, Daejeon (KR); Hyoung Jin Kim, Daejeon (KR); Heui Sul Park, Daejeon (KR); Seon Yeong Gu, Daejeon (KR); Hyo Shin Kwak, Daejeon (KR); Du Hee Park, Daejeon (KR); Hyo Soo Kim, Daejeon (KR); Hyun Jai Cho, Daejeon (KR); Ji Hyun Kim, Daejeon (KR); Ju Young Kim, Daejeon (KR); Kwang Min Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/441,998

(22) Filed: Feb. 24, 2017

(65) Prior Publication Data

US 2017/0165272 A1    Jun. 15, 2017

Related U.S. Application Data

(63) Continuation of application No. 13/503,857, filed as application No. PCT/KR2010/007344 on Oct. 25, 2010, now abandoned.

(30) Foreign Application Priority Data

Oct. 26, 2009 (KR) .................... 10-2009-0101978
Oct. 8, 2010 (KR) .................... 10-2010-0098511

(51) Int. Cl.

| | |
|---|---|
| *A61K 31/541* | (2006.01) |
| *A61K 8/49* | (2006.01) |
| *A61K 31/404* | (2006.01) |
| *C07D 417/14* | (2006.01) |
| *A61K 31/4184* | (2006.01) |
| *A61Q 19/00* | (2006.01) |
| *C07D 413/04* | (2006.01) |
| *C07D 417/04* | (2006.01) |
| *C07D 471/04* | (2006.01) |
| *C07D 487/04* | (2006.01) |
| *A61K 31/427* | (2006.01) |
| *A61K 31/496* | (2006.01) |
| *A61K 31/497* | (2006.01) |

(52) U.S. Cl.
CPC ............ *A61K 31/541* (2013.01); *A61K 8/492* (2013.01); *A61K 31/404* (2013.01); *A61K 31/4184* (2013.01); *A61K 31/427* (2013.01); *A61K 31/496* (2013.01); *A61K 31/497* (2013.01); *A61Q 19/00* (2013.01); *C07D 413/04* (2013.01); *C07D 417/04* (2013.01); *C07D 417/14* (2013.01); *C07D 471/04* (2013.01); *C07D 487/04* (2013.01); *A61K 2800/522* (2013.01)

(58) Field of Classification Search
None
See application file for complete search history.

(56) References Cited

U.S. PATENT DOCUMENTS

| | | |
|---|---|---|
| 6,420,429 B1 | 7/2002 | Atlas et al. |
| 2007/0161609 A1 | 7/2007 | Buck et al. |
| 2009/0247746 A1 | 10/2009 | Yasuma et al. |
| 2009/0291963 A1 | 11/2009 | Schadt et al. |
| 2010/0291533 A1 | 11/2010 | Kim et al. |

FOREIGN PATENT DOCUMENTS

| | | |
|---|---|---|
| WO | WO 00/31060 A1 | 6/2000 |
| WO | WO 03/082859 A1 | 10/2003 |
| WO | WO 03/087086 A2 | 10/2003 |
| WO | WO 2006/112549 A1 | 10/2006 |
| WO | WO 2006/116353 A2 | 11/2006 |
| WO | WO 2009/025477 A1 | 2/2009 |
| WO | WO 2009/025478 A1 | 2/2009 |
| WO | WO 2009/082152 A2 | 7/2009 |
| WO | WO 2009/088192 A2 | 7/2009 |

OTHER PUBLICATIONS

Chanvitayapongs et al., NeuroReport, 1997, vol. 8(6), pp. 1499-1502.*
International Search Report issued in PCT/KR2010/007344, dated Sep. 30, 2011.
Valko, M. et al, "Free radicals and antioxidants in normal physiological functions and human disease," The International Journal of Biochemistry & Cell Biology, 2007, vol. 39, pp. 44-84.

* cited by examiner

*Primary Examiner* — Savitha M Rao
*Assistant Examiner* — Gregg Polansky
(74) *Attorney, Agent, or Firm* — Rothwell, Figg, Ernst & Manbeck, P.C.

(57) ABSTRACT

The present invention relates to a pharmaceutical composition comprising a compound of formula (1), (2) or (3) as defined in the specification for the prevention or treatment of diseases associated with oxidative stress, mitochondria dysfunction, hypoxic injury, necrosis and/or ischemic reperfusion injury, and a cosmetic composition comprising an indole compound having an antioxidant effect.

2 Claims, 10 Drawing Sheets
(9 of 10 Drawing Sheet(s) Filed in Color)

a (+ vehicle)   b (+ Compound 9)

*, P<0.05 vs. Normal; **, P<0.05 vs. IR 2-way ANOVA (post-hoc), post-hoc test using Fisher's Protected Least Significant Difference (PLSD) Test Software ; StatView (v4.51, Abacus Concepts, Berkeley, CA, USA)

FDA (fluorescein diacetate)-green ; alive cells
PI (propidium iodide)-red ; necrotic cells (% in fractional shortening decrement compared with before IR injury and day 14)

Cyclosporine A 25 mg/kg   Compound 9 10 mg/kg   Compound 9 30 mg/kg a     b     c

PHARMACEUTICAL COMPOSITION COMPRISING INDOLE COMPOUND

This application is a Continuation of U.S. patent application Ser. No. 13/503,857 filed on Apr. 25, 2012, which is the National Phase of PCT/KR2010/007344 filed Oct. 25, 2010, which claims priority to Patent Application No. 10-2009-0101978 filed in Republic of Korea on Oct. 26, 2009 and Patent Application No. 10-2010-0098511 filed in Republic of Korea on Oct. 8, 2010, the entire contents of which are hereby incorporated by reference.

TECHNICAL FIELD

The present invention relates to a pharmaceutical composition comprising an indole compound for the prevention or treatment of diseases associated with oxidative stress, mitochondria dysfunction, hypoxic injury, necrosis and/or ischemic reperfusion injury, and a cosmetic composition comprising, an indole compound having an antioxidant effect.

BACKGROUND ART

Organisms including the human body obtain energy through the breathing process, and about 2% of the oxygen inhaled during metabolism is converted to reactive oxygen species (ROS) known as "oxygen toxin." The reactive oxygen species mean the oxygen containing a free radical (a generic term of atoms or molecules with unpaired electron), and generally includes lipid peroxide, lipid peroxy radical, peroxynitrite, etc. Such reactive oxygen species are known to be unstable and thus very reactive with the ambient substances to exert oxidative injuries to DNA having genetic information as well as proteins or lipid molecules in the cell, whereby ultimately fatal damage is exerted on the cell. On the other hand, in such cells of the immune system as macrophages or neutrophils, the production of reactive oxygen species is induced to play a useful role of killing pathogens that invade from the outside. Unlike in the above case and the recently recognized case wherein the reactive oxygen species play an important role in signal transduction inside the cell, the reactive oxygen species are generally recognized as causing damage to the cell and thus being harmful to organisms. Thus, in order to protect cells from the oxygen toxin, the cells themselves have antioxidants (e.g., Vitamin C, Vitamin E, small peptides such as glutathione) and antioxidant enzymes (e.g., catalase, superoxide dismutase [SOD], glutathione-dependent peroxidase [GPX], etc.).

Examples of diseases or metabolisms associated with the reactive oxygen species (ROS) or antioxidant enzymes are as follows:

1. Insulin-dependent diabetes is developed by the damage of pancreatic beta-cells, which is due to the abnormal expression of ROS.
2. Down syndrome, the subject of current clinical attention is known to be caused by the abnormality of the chromosome 21. In this case, SOD, an antioxidant enzyme, is abnormally expressed.
3. An antioxidant enzyme (catalase, glutathione-dependent peroxidase) analyzed in a cell of a progeria patient shows low enzyme activity.
4. Even in the process of converting normal cells to cancer cells, ROS is actively produced in the cells during the administration of several cancer-causing substances and irradiation.
5. Besides the above, ROS is known to be involved in atherosclerosis, Alzheimer's disease, ischemic disease, etc.

Some free radicals, reactive oxygen species and peroxides are produced during the metabolisms even in normal cells. However, the cells protect themselves against such harmful substances using antioxidant enzymes such as SOD, catalase, peroxidase, etc. as a defense system along with antioxidants such as Vitamin E, Vitamin C, glutathione, ubiquinone, uric acid, etc. When such a defense system has an abnormality or the production of reactive oxygen species exceeds the capacity of the defense system due to a variety of physical or chemical factors, however, oxidative stress is induced. If a person's disease is related to the imbalance between the oxidative stress and the antioxidative defense system in the body, theoretically the oxidative damage can be reduced or the further progress of the disease can be suppressed by adding an antioxidative substance. Thus, antioxidative functional substances such as free radical scavengers or substances inhibiting the production of peroxides are now widely used in the fields of polymers, foods, cosmetics, etc. They may also be used as an inhibitory or therapeutic agent for aging and various diseases caused by these oxides, which is based on the recent discovery that the reactive oxygen species are involved in physiological phenomena associated with the various diseases. Interest in the development of a therapeutic agent using them is increasing gradually, and the agent is actually being marketed as a health supplement in the U.S.A. with continuing popularity.

It has been demonstrated that oxidative stress is an important causative factor in inducing a variety of diseases including aging. Accordingly, the possibility of antioxidative functional substances having the ability to remove the reactive oxygen species as an agent for suppressing aging and for treating diseases is highly magnified. Thus, it is required to develop a new antioxidative functional substance that may have a function of treating aging caused by oxidative stress and a variety of diseases.

There are many antioxidants, but most of them are not effectively delivered to mitochondria and thus show a weak or little efficacy. This is why the delivery of antioxidants to mitochondria is very important in treating the above-mentioned diseases. In the case of the compound Mito Q, it was possible to be used as a therapeutic agent by conjugating coenzyme Q10 with a peptide targeting mitochondria.

On the other hand, such oxidative stress has been reported as the main mechanism of ischemic reperfusion injury. Ischemic diseases include ectomy, organ transplantation, embolization, myocardial infarction, stroke, etc.

DETAILED DESCRIPTION OF THE INVENTION

Technical Subject to be Solved

Therefore, it is an object of the present invention to provide a pharmaceutical composition comprising an indole compound useful for the prevention or treatment of diseases associated with oxidative stress mitochondria dysfunction, hypoxic injury necrosis and/or ischemic reperfusion injury, and a cosmetic composition comprising an indole compound having an antioxidant effect.

Means for Solving the Technical Subject

The present invention provides a pharmaceutical composition for the prevention or treatment of diseases associated with oxidative stress, comprising a therapeutically-effective amount of a compound of the following formula (1), (2) or (3), pharmaceutically acceptable salt or isomer thereof as an active ingredient; and a pharmaceutically acceptable carrier.

[Formula 1]

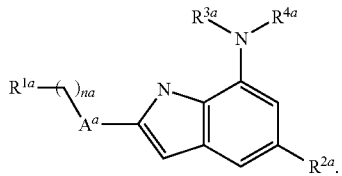

In the above formula (1), each of the substituents is concretely defined in International Patent Application Publication No. WO 2009/025477 as follows:

In formula (1),
na denotes a number of 0 to 3,
$A^a$ represents 5 membered heteroaryl or heterocycle each of which has 1 to 3 hetero atoms selected from N, O and S,
$R^{1a}$ represents $R^{5a}$—$X^a$—$B^a$—$X'^a$—,
$B^a$ represents a direct bond, or represents 3~10 membered heterocycle or heteroaryl each of which has 1 to 4 hetero atoms selected from N, O and S.
$X^a$ and $X'^a$ independently of one another represent a direct bond, or are selected from the group consisting of —$NR^{6a}$—, —CO—, —$CONR^{6a}$—, —$CO_2$—, —OC(O)—, —$S(O)_{ma}$—, —O—$(CH_2)_{ma}$—, —$(CH_2)_{ma}$—O—, —$(CH_2)_{ma}$—, —$NR^{6a}CO$—, —$(R^{6a}O)_2P(O)$— and —$NHCO_2$—, wherein ma denotes a number of 0 to 3, and $R^{6a}$ represents hydrogen, alkyl or cycloalkyl,
$R^{5a}$ represents hydrogen, nitrile, hydroxy, alkyl, alkoxy, cycloalkyl or aryl, or represents 3~10 membered monocyclic or fused cyclic heterocycle or heteroaryl each of which has 1 to 3 hetero atoms selected from N, O and S, and is optionally substituted by oxo or alkyl, or
$R^{5a}$ and $R^{6a}$ may together form a 4~8 membered cycle,
$R^{2a}$ represents —$(CR^{8a}R^{9a})_{pa}$—$Y^a$—$R^{7a}$,
pa denotes a number of 0 to 2,
$R^{8a}$ and $R^{9a}$ independently of one another represent hydrogen or alkyl, or may together form a 4~8 membered cycle,
$Y^a$ represents a direct bond, or is selected from the group consisting of —O—, —S—, —$NR^{6a}$—, —$NR^{6a}C(O)$—, —$CO_2$—, —C(O)—, —$C(O)NR^{6a}$—, —$S(O)_{qa}$—, —$S(O)_{qa}NR^{6a}$—, wherein qa denotes a number of 0 to 2,
$R^{7a}$ represents hydrogen, halogen, cyano, hydroxy, nitro, alkyl, cycloalkyl or aryl, or represents 3~10 membered heterocycle or heteroaryl each of which has 1 to 3 hetero atoms selected from N, S and O and which optionally contains oxo,
$R^{3a}$ represents hydrogen, alkyl, or —$(CH_2)_{qa}$-cycloalkyl or —$(CH_2)_{qa}$-heterocycle,
$R^{4a}$ represents —$(CH_2)_{pa}$—$D^a$—$R^{10a}$,
$D^a$ represents a direct bond, represents cycloalkyl optionally containing oxo, represents aryl, or represents 3~10 membered heterocycle or heteroaryl each of which has 1 to 3 hetero atoms selected from N, S and O,
$R^{10a}$ represents hydrogen, halogen, amino, cyano, nitro, hydroxy,alkyl, alkylcarbonyl, alkylsulfonyl or —$(CH_2)_{pa}$—$NR^{8a}R^{9a}$,
where alkyl, alkoxy, aryl, cycloalkyl, heterocycle and heteroaryl may be optionally substituted, and the substituents are one or more selected from the group consisting of hydroxy, halogen, nitrile, amino, alkylamino, dialkylamino, alkyl, haloalkyl, alkylsulfonyl, carboxyalkyl, alkylcarbonyloxy, alkylthio, alkyloxycarbonyl, alkylaminocarbonyl, arylalkoxy and oxo.

[Formula 2]

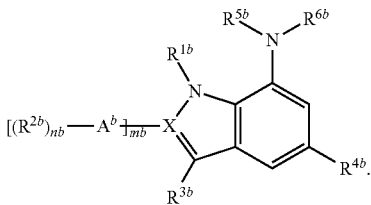

In the above formula (2), each of the substituents is concretely defined in International Patent Application Publication No. WO 2009/025478 as follows:

In formula (2),
nb denotes a number of 1 to 3,
mb denotes 0 or 1,
$A^b$ represents a direct bond, represents phenyl, or represents 6 membered heteroaryl having 1 to 2 nitrogen atoms,
$X^b$ represents C or N, with the proviso that mb is 0 when $X^b$ is N, and mb is 1 when $X^b$ is C,
$R^{1b}$ represents hydrogen, alkyl, —$(CH_2)_{rb}NR^{7b}R^{8b}$, or —$(CH_2)_{rb}CO_2H$, wherein rb denotes a number of 1 to 5, and $R^{7b}$ and $R^{8b}$ independently of one another represent hydrogen, alkyl or alkylcarbonyl, or may together form an optionally alkyl-substituted alkylene chain wherein optionally one methylene is replaced by N atom,
$R^{2b}$ represents hydrogen, halogen, cyano, nitro, hydroxy, alkyl, alkoxy or trialkylsilyl, represents —$(CH_2)_{pb}CO_2R^{7b}$, —$(CH_2)_{pb}OR^{7b}$, —$(CH_2)_{pb}NR^{7b}R^{8b}$, —$NHR^{10b}$, —N(H)S$(O)_2R^{7b}$, —$NHC(O)R^{10b}$, —$(CH_2)_{pb}S(O)_2R^{7b}$ or $(CH_2)_{pb}$-heterocycle-$R^{10b}$, wherein pb denotes a number of 0 to 3, $R^{7b}$ and $R^{8b}$ are as defined above, $R^{10b}$ represents hydrogen, oxo, alkylsulfonyl, alkylcarbonyl, alkyloxycarbonyl, alkylaminocarbonyl, alkoxy, alkyl or heterocycle,
$R^{3b}$ represents hydrogen, cyano, halogen, alkyl or phenyl, or represents —$(CH_2)_{nb}$-heterocycle or —$(CH_2)_{nb}$-aryl, wherein nb denotes a number of 0 to 3,
$R^{4b}$ represents —$Y^b R^{11b}$, wherein $Y^b$ represents a direct bond or —$(CR^{7b}R^{8b})_{pb}Y'^b$—, wherein pb denotes a number of 0 to 3, $R^{7b}$ and $R^{8b}$ are defined as above, $Y'^b$ is selected from the group consisting of —O—, —S—, —$NR^{12b}$—, —$NR^{12b}C(O)$—, —C(O)—, —C(O)O—, —$C(O)NR^{12b}$—, —$S(O)_{qb}$—, and —$S(O)_{qb}NR^{12b}$—, wherein $R^{12b}$ represents hydrogen, alkyl, aryl or heteroaryl, qb denotes a number of 0 to 2, $R^{11b}$ is selected from the group consisting of hydrogen, cyano, halogen, hydroxy, thiol, carboxy, alkyl and —$(CH_2)_{tb}B^b$—$R^{13b}$, wherein tb denotes a number of 0 to 3, $B^b$ represents heterocycle, heteroaryl or aryl, $R^{13b}$ represents hydrogen, cyano, halogen, hydroxy, oxo, thiol, carboxy, carboxyalkyl, alkylcarbonyloxy, alkyl, alkoxy, alkylthio, alkylcarbonyl or alkylsulfonyl,
$R^{5b}$ represents hydrogen, alkyl, cycloalkyl, heterocycle or heterocyclylalkyl,
$R^{6b}$ represents —$(CR^{7b}R^{8b})_{pb}$—$Z^b$—$D^b$—$W^b$—$R^{14b}$, wherein $Z^b$ represents a direct bond, or is selected from the group consisting of —C(O)—, —C(O)O—, —$C(O)NR^{12b}$—, and —$S(O)_{yb}$—, yb denotes a number of 1 or 2, $D^b$ represents a direct bond, or represents cycloalkyl, heteroaryl or heterocycle, $W^b$ represents a direct bond, or represents —$NR^{7b}$—, —C(O)—, —C(O)O—, —$C(O)NR^{12b}$—, —$S(O)_{yb}$—, —$S(O)_{yb}NR^{12b}$— or —$NR^{12b}S(O)_{yb}$—, wherein $R^{14b}$ represents hydrogen, hydroxy, alkyl, alkoxy, heterocycle, heteroaryl, aryl or aralkyl, $R^{5b}$ and $R^{6b}$ together represent alkylene chain, where alkyl, alkoxy, aryl, cycloalkyl, heterocycle and heteroaryl may be optionally substituted, and the substituents are one or more selected from the group consisting of hydroxy, halogen, nitrile, amino, alkylamino, dialkylamino, carboxy, alkyl, alkoxy, carboxyalkyl, alkylcarbonyloxy, alkylthio, alkyloxycarbonyl, alkylaminocarbonyl, arylalkoxy and oxo.

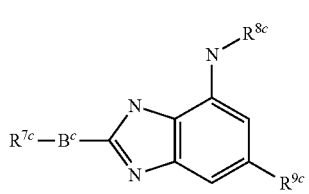

[Formula 3]

In formula (3), $B^c$ represents aryl, or represents 4~8 membered heterocycle or heteroaryl each of which has 1 to 2 hetero atoms selected from N, O and S, $R^{7c}$ represents hydrogen, halogen, hydroxy, nitrile, nitro or alkoxy, $R^{8c}$ represents $C_1$—$C_6$-alkyl, $C_3$—$C_8$-cycloalkyl, heterocyclyl, aryl, arylalkyl, cycloalkyl-alkyl or heterocyclyl-alkyl, $R_{9c}$ represents hydrogen, halogen, hydroxy, nitrile, nitro, alkoxy, allyloxy, alkylamino or arylamino, where alkyl, alkoxy, aryl, cycloalkyl, heterocycle and heteroaryl may be optionally substituted, and the substituents are one or more selected from the group consisting of hydroxy, halogen, nitrile, amino, $C_1$-$C_6$-alkylamino, di($C_1$-$C_6$-alkyl)amino, carboxy, $C_1$—$C_6$-alkyl, halogeno-$C_1$—$C_6$-alkyl, $C_1$—$C_6$-alkoxy, aryl-$C_1$—$C_6$-alkoxy and oxo.

In the above definitions for the compounds of formulas (1), (2) and (3), the term 'alkyl' means an aliphatic hydrocarbon radical. Alkyl may be saturated alkyl that does not comprise alkenyl or alkynyl moiety, or unsaturated alkyl that comprises at least one alkenyl or alkynyl moiety. "Alkenyl" means a group containing at least one carbon-carbon double bond, and "alkynyl" means a group containing at least one carbon-carbon triple bond. Alkyl may he branched or straight-chain when used alone or in a composite form such as alkoxy.

Alkyl group may have 1 to 20 carbon atoms unless otherwise defined. Alkyl group may be a medium sized alkyl having 1 to 10 carbon atoms. Otherwise, alkyl group may be a lower alkyl having 1 to 6 carbon atoms. Typical examples thereof include, but not limited to, methyl, ethyl, propyl, isopropyl, n-butyl, isobutyl, t-butyl, pentyl, hexyl, ethenyl, propenyl, butenyl, etc. For example, $C_1$—$C_4$-alkyl has 1 to 4 carbon atoms in the alkyl chain, and is selected from the group consisting of methyl, ethyl, propyl, isopropyl, n-butyl, iso-butyl, sec-butyl and t-butyl.

The term 'alkoxy' means an alkyloxy having 1 to 10 carbon atoms unless otherwise defined.

The term 'cycloalkyl' means a saturated aliphatic 3~10 membered cycle unless otherwise defined. Typical examples thereof include, but not limited to, cyclopropyl, cyclobutyl, cyclopentyl cyclohexyl, etc.

The term 'aryl' includes at least one ring having covalent π electron system, for example, monocyclic or fused polycyclic (i.e., cycles that share the adjacent carbon atom pairs) groups. In the present specification, aryl means an aromatic 4~10 membered, preferably 6~10 membered, monocyclic or multicyclic ring including phenyl, naphthyl, etc., unless otherwise defined.

The term 'heteroaryl' means an aromatic 3~10 membered, preferably 4~8 membered, more preferably 5~6 membered cycle that has 1 to 4 hetero atoms selected from N, O and S, and may be fused with benzo or $C_3$—$C_8$ cycloalkyl, unless otherwise defined. The monocyclic heteroaryl includes, but not limited to, thiazole oxazole, thiophene, furan, pyrrole, imidazole, isoxazole, isothiazole, pyrazole, triazole, triazine, thiadiazole, tetrazole, oxadiazole, pyridine, pyridazine, pyrimidine, pyrazine and the like. The bicyclic heteroaryl includes, but not limited to, indole, indoline, benzotbiophene, benzofuran, benzimidazole, benzoxazole, benzisoxazole, benzthiazole, benzthiadiazole, benztriazole, quinoline, isoquinoline, purine, puropyridine and the like.

The term 'heterocycle' means a 3~10 membered, preferably 4~8 membered, more preferably 5~6 membered cycle that has 1 to 4 hetero atoms selected from N, O and S, may he fused with benzo or $C_3$—$C_8$ cycloalkyl, and is saturated or contains 1or 2 double bonds, unless otherwise defined. The heterocycle includes, but not limited to, pyrroline, pyrrolidine, imidazoline, imidazolidine, pyrazoline, pyrazolidine, pyran, piperidine, morpholine, thiomorpholine, piperazine, hydrofuran and the like.

Other terms and abbreviations in the present specification may be understood to have the meaning conventionally used in this field by a skilled artisan, unless otherwise defined.

Preferred examples of the compounds of formula (1) or (2) may be listed as follows:

Compound 1: [(S)-2-(7-cyclopentylamino-5-methyl-1H-indol-2-yl]-4,5-dihydro-thiazol-4-yl]-acetic acid Compound 2: {(S)-2-[5-methyl -7-(tetrahydropyran-4-ylamino)- 1H-indol-2-yl]-4,5-dihydro-thiazol-4-yl}-acetic acid Compound 3: [(S)-2-(7-cyclopentylamino-5-methyl-1H-indol-2-yl)-4,5-dihydro-oxazol-4-yl]-acetic acid Compound 4: [(S)-2-(7-cyclopentylamino-1H-indol-2-yl)-4,5-dihydro-thiazol-4-yl]-acetic acid Compound 5: [(S)-2-(7-cyclopentylamino-5-phenoxy-1H-indol-2-yl)-4,5-dihydro-thiazol-4-yl]-acetic acid Compound 6: 4-{2-[(S)-2-(7-cyclopentylamino-5-phenoxy- 1H-indol-2-yl)-4,5-dihydro-thiazol-4-yl]-ethyl}-piperazin-2-one Compound 7: cyclopentyl-(2-{(S)-4-[2-(3-methyl-5,6-dihyro-8H-[1,2,4]triazolo[4,3-a]pyrazin-7-yl)-ethyl]-4,5-dihydro-thiazol-4-yl}-5-phenoxy-1H-indol-7-yl)-amine Compound 8: ((S)-2-{7-[(tetrahydropyran-4-ylmethyl)-amino]-1H-indol-2-yl}-4,5-dihydro-thiazol-4-yl)-acetic acid Compound 9: (tetrahydropyran-4-yl)-[2-phenyl-5-(1,1-dioxo-thiomorpholin-4-yl)methyl-1H-indol-7-yl]-amine Compound 10: [5-(1,1-dioxo-thiomorpholin-4-yl)methyl-2-phenyl-1H-indol-7-yl]-(tetrahydropyran-4-yl)methyl-amine Compound 11: [5-(1,1-dioxo-thiomorpholin-4-yl)methyl-2-phenyl-1H-indol-7-yl]-bis-[(tetrahydropyran-4-yl) methyl]-amine Compound 12: {4-[5-(1,1-dioxo-thiomorpholin-4-yl) methyl-2-phenyl-1H-indol-7-ylamino]-piperidin-1-yl}-(tetrahydropyran-3-yl)methanone Compound 13: [5-(1,1-dioxo-thiomorpholin-4-yl)methyl-2-phenyl-1H-indol-7-yl]-(1-methylsulfonyl-piperidin-4-yl)-amine Compound 14: ((S)-2-{5-methyl-7-[(tetrahydropyran-4-ylmethyl)-amino]-1H-indol-2-yl}-4,5-dihydro-thiazol-4-yl)-acetic acid Preferred compounds among the compounds of formula (3) above are those wherein $B^c$ represents, aryl, or represents 5~6 membered heterocycle or heteroaryl each of which has 1to 2 hetero atoms selected from N, O and S, $R^{7c}$ represents hydrogen, halogen, nitrile or alkoxy, $R^{8c}$ represents $C_1$—$C_6$-alkyl, $C_3$—$C_8$-cycloalkyl, heterocyclyl, arylalkyl, cycloalkyl-alkyl or heterocyclyl-alkyl, $R^{9c}$ represents hydrogen, halogen, nitrile, alkoxy, allyloxy, alkylamino or arylamino.

More preferably, in formula (3), $B^c$ represents phenyl or pyridine.

More preferably, in formula (3) $R^{7c}$ represents hydrogen, halogen or alkoxy, and most preferably, hydrogen.

More preferably, in formula (3), $R^{8c}$ represents $C_1$—$C_6$-alkyl, heterocyclyl, heterocyclyl-alkyl or arylalkyl, and most preferably, cyclopentyl or tetrahydropyran.

More preferably, in formula (3), $R^{9c}$ represents hydrogen, halogen or alkoxy, and most preferably, hydrogen.

The representative compounds of formula (3) include the following:
cyclopentyl-(2-phenyl-3H-benzimidazol-4-yl)-amine
(2-phenyl-3H-benzimidazol-4-yl)-(tetrahydro-pyran-4-yl)-amine
cyclopentyl-(2-pyridin-2-yl-3H-benzimidazol-4-yl)-amine The pharmaceutical composition of the present invention can be effectively used for the prevention and treatment of disease caused by oxidative stress.

The pharmaceutical composition of the present invention can be effectively used for the prevention and treatment of disease caused by oxidative stress which is mediated by reactive oxygen species (ROS) or reactive nitrogen species (RNS).

The pharmaceutical composition of the present invention can suppress ischemic reperfusion injury.

The pharmaceutical composition of the present invention can be effectively used for the prevention and treatment of disease caused by hypoxic injury.

The pharmaceutical composition of the present invention can be effectively used for the prevention and treatment of disease caused by necrotic cell death.

The pharmaceutical composition of the present invention can suppress mitochondrial dysfunction.

The pharmaceutical composition of the present invention can be effectively used for the prevention and treatment or MELAS caused by mitochondrial dysfunction (mitochondrial myopathy, encephalopathy, lactic acidosis and stroke-like episodes), MERRF syndrome (myoclonus epilepsy with ragged-red fibers) or Kearns-Sayre syndrome all of which are caused by mitochondrial dysfunction.

The pharmaceutical composition of the present invention can suppress necrosis of cells secreting HMGB1 (high-motility group box 1).

Furthermore, the pharmaceutical composition of the present invention can prevent and/or treat a disease mediated by HMGB1, in particular an inflammation-mediated or -related disease. Such diseases include sepsis, rheumatic arthritis, osteoarthritis, liver cirrhosis, hemorrhagic disease, various necrotizing diseases, virus or bacteria infection, etc.

The diseases to be prevented and/or treated by the present invention include liver disease, heart disease, vascular disease, degenerative brain disease, disease caused by ischemic reperfusion injury, and infectious disease by virus or bacteria; liver transplantation, hepatic resection, hepatic embolization, hepatic fibrosis, hepatic cirrhosis, alcoholic/non-alcoholic fatty liver, and hepatitis caused by virus or drug (e.g., anticancer agent, acetaminophen, etc.); heart or cardiovascular diseases such as arrhythmia, cardioplegia, myocardial infarction, etc.; degenerative brain diseases such as Lou Gehrig's disease, stroke, dementia, Parkinson's disease, Huntington's disease, etc.; diabetic complex, arteriosclerosis, myocardial infarction or stroke, each of which is caused by ischemic reperfusion injury; disease caused by infection of a virus such as influenza, HBV, HCV, HIV, etc. or bacteria.

In the present invention, the liver disease ma be one or more selected from the group consisting of liver transplantation, hepatic resection, hepatic embolization, hepatic fibrosis, hepatic cirrhosis, alcoholic/non-alcoholic fatty liver, and hepatitis caused by virus or drug (e.g., anticancer agent, acetaminophen, etc.).

In the present invention, the heart or cardiovascular disease may be one or more selected from the group consisting of arrhythmia, cardioplegia, myocardial infarction, heart failure and angina pectoris.

The pharmaceutical composition of the present invention can be effectively used for the prevention and treatment of liver disease, heart or cardiovascular disease, each of which is caused by ischemic reperfusion injury, wherein the ischemic reperfusion injury may result from mitochondrial dysfunction, hypoxic injury and/or necrotic cell death.

The pharmaceutical composition of the present invention can be effectively used for the prevention and treatment of one or more diseases selected from the group consisting of diabetic complex, arteriosclerosis and stroke, each of which is caused by ischemic reperfusion injury.

Specific embodiments of synthesis of the compounds of Formula (1) or (2) of the present invention are disclosed in WO 2009/025477 and WO 2009/025478, respectively.

The present invention also provides the compounds of Formula (3) and the processes for preparing the same. Hereinafter, the processes for preparing the compounds of Formula (3) will be explained based on exemplary reaction schemes in order to help understanding of the present invention. However, it should be understood that a person having ordinary skill in the art could prepare the compounds of Formula (3) by various methods on the basis of the structure of Formula (3) and all such methods fall within the scope of the present invention. In other words, it should be understood that the compounds of Formula (3) can be prepared through any combination of various synthesis methods described herein or disclosed in prior arts and such combination falls within the scope of the present invention. The processes for preparing the compounds of Formula (3) are not limited to those described below.

First, the compounds of Formula (3) can be synthesized by reducing the nitro group of the compounds of Formula (4) to give the amine compounds of Formula (5) and carrying out a reductive amination (RA) reaction on the formed amine group with the compounds of Formula (6), according to the method shown in the following Reaction Scheme 1.

Reaction Scheme 1

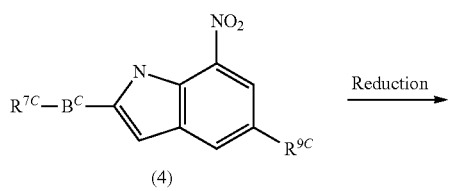

(4)

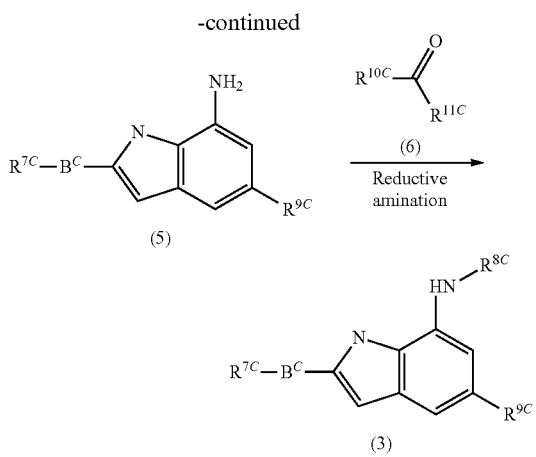

wherein

B$^c$, R$^{7c}$, R$^{8c}$ and R$^{9c}$ are as defined in Formula (3);

R$^{10c}$ represents alkyl, cycloalkyl, heterocyclyl, heteroaryl or aryl;

R$^{11c}$ represents hydrogen or alkyl; or

R$^{10c}$ and R$^{11c}$ can cyclize to form cycloalkyl or heterocycle.

The compounds of Formula (5) can be prepared by reduction of the compounds of Formula (4). Reduction reactions can be carried out using acid catalysts and metals or using metal catalysts under the presence of hydrogen gas.

Examples of acid that can be used for the reduction reaction which involves the use of acid catalysts and metals include inorganic acid such as hydrochloric acid, sulfuric acid, nitric acid and phosphoric acid; organic carbonic acid such as acetic acid and trifluoroacetic acid; and salt of amine acid such as ammonium chloride, Preferable acids are hydrochloric acid, acetic acid, ammonium chloride, etc. The amount of acids to be used is typically 0.01 to 10 equivalents and preferably 0.1 to 5 equivalents, to 1 equivalent of the compounds of Formula (4). Examples of metal that can be used include iron, zinc, lithium, sodium and tin (generally, tin chloride). Preferable metals are iron, zinc, tin chloride, etc. The amount of metals to be used is typically 1 to 20 equivalents and preferably 1 to 10 equivalents, to 1 equivalent of the compounds of Formula (4). Metal reactions under the presence of acid catalysts can be carried out in an inert solvent. Examples of inert solvent include alkyl alcohol such as methanol and ethanol; ether such as tetrahydrofuran and diethylether; and alkyl ester such as ethylacetate. Preferable solvents are methanol, ethanol, tetrahydrofuran and ethylacetate, etc. Reaction temperature is typically −10 to 200□ and preferably 25 to 120□. Reaction time is typically 10 min to 60 hours and preferably 10 min to 12 hours.

Examples of metal catalyst that can be used for the reduction reaction which involves the use of metal catalysts under the presence of hydrogen gas include palladium, nickel, platinum, ruthenium, rhodium and the like. Preferable metal catalysts are palladium, nickel, etc. The amount of metal catalysts to be used is typically 0.001 to 2 equivalents and preferably 0.01 to 1 equivalents, to 1 equivalent of the compounds of Formula (2). Pressure of hydrogen gas is typically 1 to 10 atm, and preferably 1 to 3 atm. Reactions can be carried out in an inert solvent, for example alkyl alcohol such as methanol and ethanol ether such as tetrahydrofuran and diethylether; and alkyl acetate such as methylacetate and ethylacetate. Preferable solvents are methanol, ethanol, ethylacetate, etc. In the reduction reaction which involves the use of metal catalysts, reaction temperature is typically −10 to 200□ and preferably 25 to 50□. Reaction time is typically 10 min to 60 hours and preferably 10 min to 12 hours.

The compounds of Formula (6) are commercially available and can be prepared through a reductive amination reaction of the amine group of the compounds of Formula (5).

Reductive amination reaction can be carried out through reaction of aldehyde or ketone with a reducing agent, and an acid catalyst, if necessary. The amount of aldehyde or ketone to be used is typically 1 to 10 equivalents and preferably 1 to 3 equivalents, to 1 equivalent of the compounds of Formula (5). Examples of reducing agent that can be used include sodium borohydride, sodium cyanoborohydride (NaBH$_3$CN) and sodium triacetoxy-borohydride {NaBH(OAc)$_3$}. The amount of reducing agents to be used is typically 1 to 10 equivalents and preferably 1 to 3 equivalents, to 1 equivalent of the compounds of Formula (5). Examples of acid catalyst that can be used include inorganic acid such as hydrochloric acid, sulfuric acid, nitric acid and phosphoric acid; organic carbonic acid such as acetic acid and trifluoroacetic acid; and salt of amine acid such as ammonium chloride. Preferable acids are hydrochloric acid, acetic acid, etc. The amount of acids to be used is typically 0.1 to 10 equivalents and preferably 1 to 5 equivalents, to 1 equivalent of the compounds of Formula (5). Reactions can be carried out in an inert solvent, for example ether such as tetrahydrofuran and diethylether; and chloroalkane such as dichloromethane, chloroform and dichloroethane, and preferably dichloroethane, chloroform, etc. Reaction temperature is typically −10 to 100□ and preferably −10 to 50□. Reaction time is typically 10 min to 60 hours add preferably 10 min to 12 hours.

The compounds of Formula (4) can be prepared by linking reaction and cyclization reaction of the aldehyde compounds of Formula (7) with the compounds of Formula (8), as shown in the following Reaction Scheme 2.

Reaction Scheme 2

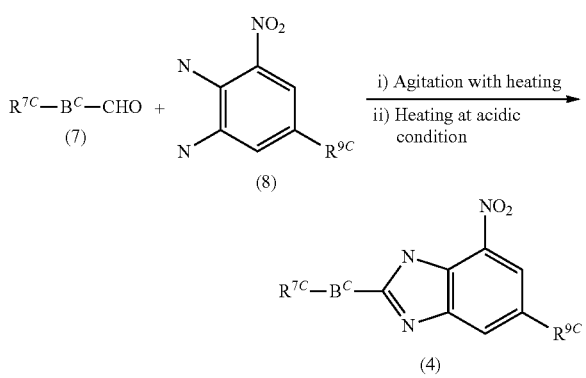

wherein B$^c$, R$^{7c}$ and R$^{9c}$ are as defined Formula (3).

First, commercially available aldehydes such as the compounds of Formula (7) and commercially available diamine compounds such as the compounds of Formula (8) are heated with stirring to form a cyclization. Then, heating under the presence of acid catalysts could give the compounds of Formula (4). Examples of acid catalyst that can be used include inorganic acid such as hydrochloric acid, sulfuric acid, nitric acid and phosphoric acid; organic carbonic acid such as acetic acid and trifluoroacetic acid; and salt of amine acid such as ammonium chloride. Preferable acid catalysts are hydrochloric acid, acetic acid, etc. The amount of acids to be used is typically 0.1 to 10 equivalents, and preferably 1 to 5 equivalents, to 1 equivalent of the compounds of Formula (5). Depending on the case, reactions can be carried out using organic acids such as acetic acid as a solvent.

In the present specification, "pharmaceutically acceptable salt" includes non-toxic acid addition salt containing pharmaceutically acceptable anion, for example, a salt with inorganic acids such as sulfuric acid, hydrochloric acid, nitric acid, phosphoric acid, hydrobromic acid, hydriodic acid, etc.: a salt with organic carboxylic acids such as tartaric acid, formic acid, citric acid, acetic acid, trichloroacetic acid, trifluoroacetic acid, gluconic acid, benzoic acid, lactic acid, fumaric acid, maleic acid, salicylic acid, etc.; or a salt with sulfonic acids such as methanesulfonic acid, ethanesulfonic acid, benzenesulfonic acid, p-toluenesulfonic acid, naphthalenesulfonic acid, etc. The compounds of formula (1) can also form a pharmaceutically acceptable base addition salt, for example, a salt with alkali metals or alkaline earth metals such as lithium, sodium, potassium, calcium, magnesium, etc.; a salt with amino acids such as lysine, arginine, guanidine, etc.; or an organic salt with dicyclohexylamine, N-methyl-D-glucamine, tris(hydroxymethyl)methylamine, diethanolamine, choline, triethylamine, etc. The compounds of formulas (1), (2) and (3) of the present invention may be converted to their salts according to any of the conventional methods, and the salt formation can be easily carried out by a skilled artisan based on the structure formulas (1), (2) and (3) without additional explanations thereon.

The term "isomer" in the present specification means those having the same chemical or molecular formula as, but optically or sterically different from, the compounds of formula (1), or salts thereof. The compounds of formulas (1), (2) and (3) of the present invention may have an asymmetric carbon center(s) in the structure, and so may exist in the form of optical isomer (R or S isomer), racemate, mixture of diastereomers, or individual diastereomer, etc. When the compounds have a double bond, they may exist in the form of geometric isomer (trans or cis isomer). All the isomers and their mixtures are also covered by the present invention, Hereinafter, the compounds of formulas (1), (2) and (3) include pharmaceutically acceptable salts and isomers thereof, unless otherwise explained. The salts and isomers should be construed to be covered by the present invention. For the sake of convenience, the present specification briefly expresses them as the compounds of formula (1).

The above-mentioned "pharmaceutical composition" may comprise pharmaceutically acceptable carriers, diluents, excipients, or their combinations, if needed, together with the compounds of the present invention. Pharmaceutical composition facilitates the administration of the compound into a living, organism. There exist a number of techniques to administer the compound, and they include, but not limited to, oral, injectable, aerosol, parenteral and topical administration.

As used herein, "carrier" means a substance which facilitates the incorporation of the compound into the cells or tissues. For example, dimethylsulfoxide (DMSO) is a typical carrier which is used to facilitate the introduction of various organic compounds into the cells or tissues of living organisms.

As used herein, "diluent" is defined as a substance that is diluted in water which dissolves the compound, as well as stabilizes the biologically active form of the subject compound. The salts dissolved in buffer solution are utilized as diluents in the art. Typically used buffer solution is phosphate buffered saline which mimics the salt form of human solution. Buffer diluents rarely alter the biological activities of the compound, as the buffer salts can control the pH of solution at low concentration.

As used herein, "pharmaceutically acceptable" means the property that does not impair the biological activities and physical properties of the compound.

The compounds of the present invention can be formulated as various pharmaceutical dosage forms according to the desired purpose. For the preparation of the pharmaceutical composition of the present invention, active ingredient, specifically, the compounds of formula (1), (2) or (3), pharmaceutically acceptable salts or isomers thereof are mixed together with various pharmaceutically acceptable carriers which can be selected according to the formulation to be prepared. For example, the pharmaceutical composition of the present invention can be formulated as injectable preparation, oral preparation, etc., according to the desired purpose.

The compounds of the present invention can be formulated by the methods known in the art, which utilize pharmaceutical carriers and excipients known in the art, and be incorporated into the containers of unit dose form or multdose form. The form of the preparation can be solutions, suspensions or emulsions in oily or aqueous media, and contain typical dispersing agents, suspending agents or stabilizers. Further, for example, it can be a form of dry powder which is intended to be reconstituted by dissolving in sterile, pyrogen-free water prior to use. The compounds of the present invention also can be formulated into suppository forms utilizing typical suppository base such as cocoa butter or other glycerides. As solid dosage forms for oral administration, capsules, tablets, pills, powder and granule can be prepared, and capsules and tablets are especially useful. Preferably, tablets and pills are prepared as enteric coated forms. Solid dosage forms can be prepared by mixing the compounds of the present invention together with carriers such as one or more inert diluents such as sucrose, lactose, starch, etc., lubricants such as magnesium stearate, disintegrants, binders, etc.

The present invention also provides a cosmetic composition having an antioxidant effect, comprising a compound of aforesaid formula (1), (2) or (3), pharmaceutically acceptable salt or isomer thereof as an active ingredient; and an acceptable carrier.

Effect of Invention

The pharmaceutical composition of the present invention has an excellent antioxidant activity and thus can effectively prevent or treat various diseases associated with oxidative stress.

In addition, the pharmaceutical composition of the present invention can effectively prevent or treat heart or cardiovascular diseases by suppressing mitochondria dysfunction in cardiac muscle cells, hypoxic injury, necrosis and ischemic reperfusion injury. In addition, it can be used as a heart protecting agent in reperfusion treatments such as operation therapies including coronary artery bypass grafts or percutaneous transluminal coronary angioplasty and drug therapies using thrombolysis agents or the like.

The patent or application file contains at least one drawing executed in color. Copies of this patent or patent application publication with color drawing(s) will be provided by the office upon request and payment of the necessary fee.

CONCRETE EMBODIMENTS TO CARRY OUT THE INVENTION

Figure 1:
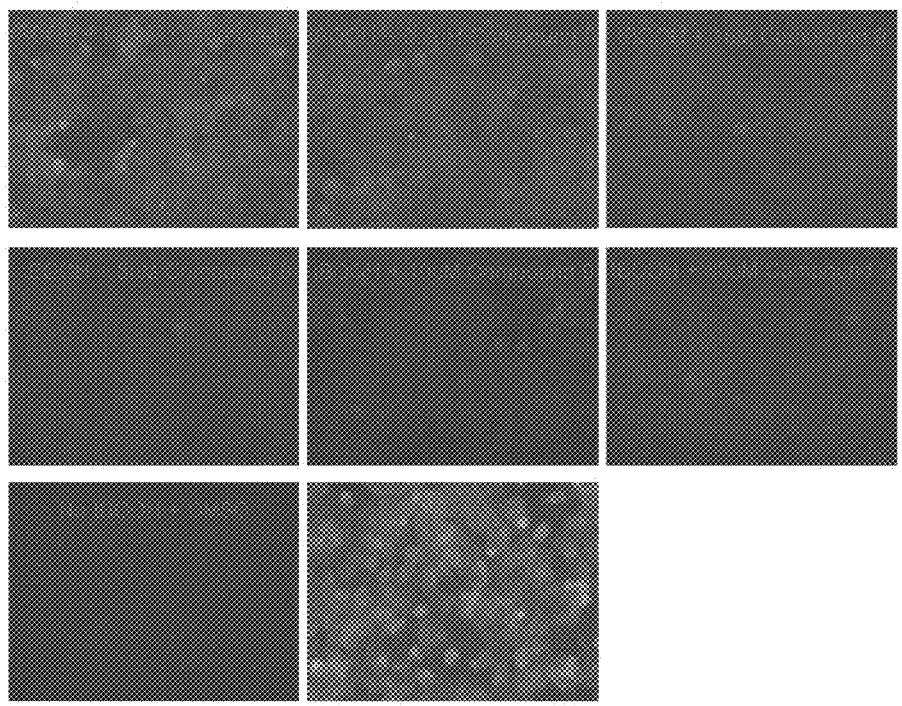
FIG. 1 is a photograph showing the anti-oxidant effect of (tetrahydropyran-4-yl)-[2-phenyl-5-(1,1-dioxo-thiomorpholin-4-yl)methyl-1H-indol-7-yl]-amine (Compound 9) in a cell by using DHR123 probe.
Figure 2:
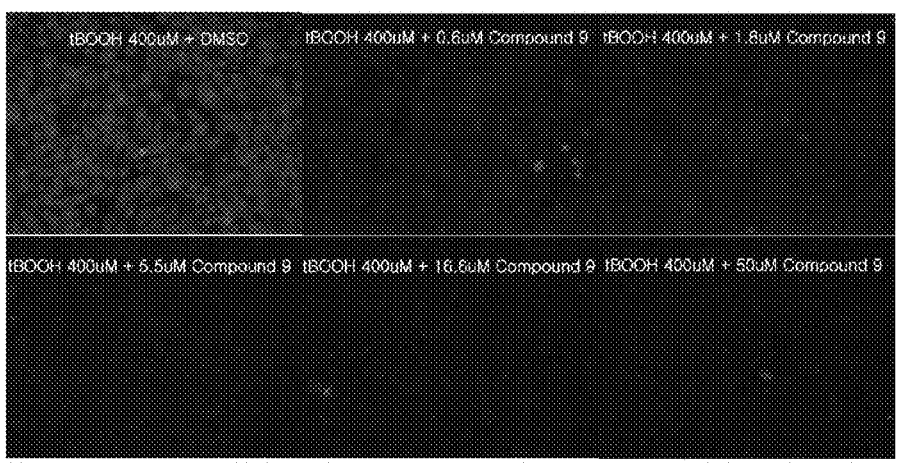
FIG. 2 is a photograph showing the anti-oxidant effect of Compound 9 in a cell by using MitoSOX red probe.

Hereinafter, the present invention will be described in more detail with reference to the following examples, but the scope of the present invention should not be construed to be limited thereby in any manner.

EXAMPLE 1

Preparation of cyclopentyl-(2-phenyl-3H-benzoimidazole-4-yl)-amine

Step A: 4-Nitro-2-phenyl-2,3-dihydro-1H-benzoimidazole

To a solution of 3-nitro-benzene-1,2-diamine 1.0 g (6.5 mmol) in methanol (10 mL) was added benzaldehyde 0.69 g (6.7 mmol) and stirred at 80□ for 2 days. After completion of the reaction, the solvent was removed in vacuo, and the residue was purified by column chromatography to give the title compound 1.1 g (yield: 70%).

$^1$H-NMR (500 HMz, DMSO); δ8.68 (s, 1H), 7.43~7.31 (m, 5H), 7.18 (s, 1H), 6.95 (d, 1H), 6.44 (s, 1H), 6.36 (t, 1H), 6.29 (d, 1H)

Step B: 7-Nitro-2-phenyl-1H-benzoimidazole 4-nitro-2-phenyl-2,3-dihydro-1H-benzoimidazole 1.1 g (4.6 mmol) obtained in Step A was dissolved in acetic acid (10 mL) and stirred at 80□ for 3 hours. After completion of the reaction, water was added, extracted with ethyl acetate and washed with 1N-sodium hydroxide. After drying with anhydrous magnesium sulfate, the filtrate was distilled in vacuo, and the residue was purified by column chromatography to give the title compound 0.91 g (yield: 83%).

$^1$H-NMR (400 HMz, DMSO); δ13.3 (br s, 1H), 8.37 (d, 2), 8.15 (d, 2H), 7.65~7.56 (m, 3H), 7.46 (t, 1H)

Step C: 2-Phenyl-3H-benzoimidazole-4-ylamine 7-nitro-2-phenyl-1H-benzoimidazole 0.137 g (0.57 mmol) obtained in Step B was dissolved in tetrahydrofuran (5 mL), methanol (5 mL) and water (5 mL). To the solution was added iron powder 0.40 g (7.2 mmol) and ammonium chloride 0.39 g (7.2 mmol) and stirred at 60□ for 1 hour. After completion of the reaction, water was added and extracted with ethyl acetate. After drying with anhydrous magnesium sulfate, the filtrate was distilled in vacuo, and the residue was purified by column chromatography to give the title compound 0.12 g (yield: 79%).

$^1$H-NMR (500 HMz, DMSO); δ12.5 (s, 1H), 8.10 (d, 2H), 7.55~7.45 (m, 3H), 6.87 (t, 1H), 6.67 (d, 1H), 6.32 (d, 1H), 5.21 (s, 2H)

Step D: Cyclopentyl-(2-phenyl-3H-benzoimidazole-4-yl)-amine 2-phenyl-3H-benzoimidazole-4-ylamine 0.040 g (0.19 mmol) obtained in Step C was dissolved in dichloroethane (5 mL). To the solution was added acetic acid 0.012 mg (0.19 mmol), cyclopentaneon 0.048 g (0.57 mmol) and sodium triacetoxy-borohydride 0.049 mg (0.23 mmol), and stirred at room temperature for 18 hours. After completion of the reaction, water was added, extracted with dichloromethane and washed with a saturated sodium chloride solution. After drying with anhydrous magnesium sulfate, the filtrate was distilled in vacuo, and the residue was purified by column chromatography to give the title compound 0.026 mg (yield: 49%).

$^1$H-NMR (40 HMz, CDC13); δ9.36 (br s, 1H), 8.02 (m, 2H), 7.56~7.45 (m, 3H), 7.17 (t, 1H), 6.83 (d, 1H), 6.47 (d, 1H) 5.06 (br s, 1H), 4.02 (m, 1H), 2.13 (m, 2H), 1.82 (m, 2H), 1.69 (m, 4H)

EXAMPLE 2

Preparation of (2-phenyl-3H-benzimidazole-4-yl)-(tetrahydrofuran-4-yl)-amine

Using 2-phenyl-3H-benzoimidazole-4-ylamine 0.040 g (0.19 mmol) obtained in Step C of Example 1 and tetrahydrofuran-4-carbaldehyde 0.026 g (0.23 mmol), the title compound 0.030 mg (yield: 51%) was prepared according to the same method as described in Step D of Example 1.

$^1$H-NMR (40 HMz, CDC13); δ8.02 (m, 2H), 7.56~7.45 (m, 3H), 7.17 (t, 1H), 6.85 (d, 1H), 6.44 (d, 1H) 4.05 (dd, 1H), 3.45 (td, 2H), 3.27 (d, 1H), 2.02 (m, 1H), 1.85 (m, 2H), 1.45 (m, 2H)

EXAMPLE 3

Cyclopentyl-(2-phenyl-2-yl-3H-benzoimidazole-4-yl)-amine

Using 2-carboxy aldehyde, 3-nitro-benzene-1,2-diamine and cyclopentanone, the title compound was prepared according to the same method as described in Example 1.

$^1$H-NMR (40 HMz, CDC13); δ1.64 (m, 6H), 2.10 (m, 2H), 4.14 (s, 1H), 6.38~6.34 (d, 1H), 6.69~6.71 (d, 1H), 7.09~7.13 (t, 1H), 7.25~7.26 (m, 1H), 7.75~7.79 (m, 1H), 8.40~8.41 (d, 1H), 8.54~8.55 (m, 1H).

The effect of the present invention is illustrated concretely by the experimental examples below. The compounds used in the experimental examples are as follows.

Compound 1: [(S)-2-(7-cyclopentylamino-5-methyl-1H-indol-2-yl)-4,5-dihydro-thiazol-4-yl]-acetic acid Compound 2: {(S)-2-[5-methyl-7-(tetrahydropyran-4-ylamino)-1H-indol -2-yl]-4,5-dihydro-thiazol-4-yl}-acetic acid Compound 3: [(S)-2-(7-cyclopentylamino-5-methyl-1H-indol-2-yl)-4,5-dihydro-oxazol-4-yl]-acetic acid.

Compound 4: [(S)-2-(7-cyclopentylamino-1H-indol-2-yl)-4,5-dihydro-thiazol-4-yl]-acetic acid Compound 5: [(S)-2-(7-cyclopentylamino-5-phenoxy-1H-indol-2-yl)-4,5-dihydro-thiazol-4-yl]-acetic acid Compound 6: 4-{2-[(S)-2-(7-cyclopentylamino-5-phenoxy-1H-indol-2-yl)-4,5-dihydro-thiazol-4-yl]-ethyl}-piperazin-2-one Compound 7: cyclopentyl-(2-{(S)-4-[2-(3-methyl-5,6-dihydro-8H-[1,2,4]triazolo[4,3-a]pyrazin-7-yl)-ethyl]-4,5-dihydro-thiazol-4-yl}-5-phenoxy- 1H-indol-7-yl)-amine Compound 8: ((S)-2-{7-[(tetrahydropyran-4-ylmethyl)-amino]-1H-indol-2-yl}-4,5-dihydro-thiazol-4-yl)-acetic acid Compound 9: (tetrahydropyran-4-yl)-[2-phenyl-5-(1,1-dioxo-thiomorpholin-4-yl)methyl-1H-indol-7-yl]-amine Compound 10: [5-(1,1-dioxo-thiomorpholin-4-yl)methyl-2-phenyl-1H-indol-7-yl]-(tetrahydropyran-4-yl)methyl-amine Compound 11: [5-dioxo-thiomorpholin-4-yl)methyl-2-phenyl-1H-indol-7-yl]-bis-[(tetrahydropyran-4-yl)methyl]-amine Compound 12: {4-[5-(1,1-dioxo-thiomorpholin-4-yl)methyl-2-phenyl-1H-indol-7-ylamino]-piperidin-1-yl}-(tetrahydropyran-3-yl)methanone Compound 13: [5-(1,1-dioxo-thiomorpholin-4-yl)methyl-2-phenyl-1H-indol-7-yl](1-methylsulfonyl-piperidin-4-yl)-amine Compound 14: ((S)-2-{5-methyl-7-[(tetrahydropyran-4-ylmethyl)-amino]-1H-indol-2-yl}-4,5-dihydro-thiazol-4-yl)-acetic acid Example 1: cyclopentyl-(2-phenyl-3H -benzimidazol-4-yl)- amine Example 2: (2-phenyl-3H-benzimidazol-4-yl)-(tetrahydro-pyran-4-yl)-amine

EXPERIMENTAL EXAMPLE 1

Anti-oxidant Effects of Necrosis Inhibitors

To measure the anti-oxidant effect of each compound, the following experiments were carried out: The DPPH method to measure total anti-oxidant effect, a method of measuring anti-oxidant effect by using dihydrorhodamine 123, a method of measuring necrosis inhibition by using tBOOH which causes oxidative stress to cells, a method of measuring the removal capacity of $ONOO^{31}$ (peroxynitrite), and a direct method of measuring anti-oxidant effects on $H_2O_2$ (hydrogen peroxide) and tBOOH.

EXPERIMENTAL EXAMPLE 1-1

Measurement of Anti-oxidant Effect by Using DPPH

DPPH (1,1-diphenyl-2-picrylhydrazyl) is a stable free radical and has a purple color. The anti-oxidant effect of compound was measured by using a principle in which the color of DPPH is changed to yellow when DPPH is reduced by a compound. DPPH shows strong absorbance at 517 nm, and when DPPH is reduced, the color is changed to yellow and absorbance at 517 nm is decreased. Herein, the term "$IC_{50}$" refers to the concentration of a compound which decreases absorbance at 517 nm to 50% of the original value.

180 μl of DPPH solution (200 μM in DMSO) was dispensed into each well of a 96-well plate, and 20 μl of compounds, which was serially diluted two-fold from 2,000 μM, was added thereto. They were then well mixed and kept at room temperature for 30 minutes. After 30 minutes, O.D. value at 517 nm was measured with a spectraMAX ELISA reader. The results are represented in the following Table 1.

TABLE 1

| Compound Number | DPPH anti-oxidant effect ($IC_{50}$, μM) |
| --- | --- |
| Compound 1 | 24 |
| Compound 2 | 24 |
| Compound 3 | 17.5 |
| Compound 4 | 15 |
| Compound 5 | 20 |
| Compound 6 | 23 |
| Compound 7 | 25 |
| Compound 8 | 20.5 |
| Compound 9 | 16 |
| Compound 10 | 22 |
| Compound 11 | 12.5 |
| Compound 12 | 19 |
| Compound 13 | 17 |
| Compound 14 | 28 |

EXPERIMENTAL EXAMPLE 1-2

Measurement of Anti-oxidant Effect by Using dihydrorhodamine 123

Dihydrorhodamine 123 itself is nonfluorescent but is converted to fluorescent rhodamine 123 when it is oxidized by ROS (reactive oxygen species) or RNS (reactive nitrogen species). Anti-oxidant effects of compounds in cells or in vitro were measured by using such a property. H9C2 cells were dispensed into each well of a 96-well plate ($1.5 \times 10^4$ cells/100 μl/well). The next day, the cells were pretreated with each compound, which was serially diluted 3-fold from the highest concentration, for 1 hr, and then treated with 10 µl of DHR123 12.5 µM stock solution (final concentration: 1.25 µM) in 37° C. incubator for 30 minutes. The cells were then immediately treated with 400 µM tBOOH and incubated for 2 hrs. Then, fluorescence, which was excited at 480 nm and emitted at 538 nm, was measured with a spectraMAX Gemini microplate reader. Herein, the term "$IC_{25}$" refers to the concentration of a compound which causes 25% inhibition of value in which fluorescence of 2 hrs after tBOOH treatment, which was emitted by oxidation of DHR123 due to the increase of oxidative stress, was defined as 100%. The results are represented in Table 2. In addition, to check whether the compounds actually have an anti-oxidant effect on cells, after the above assay cells in the 96-well plate were fixed with 4% formaldehyde and washed three times with. PBS. Then 100 µl of PBS was added to each well of the 96-well plate and fluorescence of each cell was measured by immunofluorescence microscopy (fluorescence microscope: Olympus) (Because of DHR123 in cells, fluorescence is emitted in proportion to oxidation). The results are shown in FIG. 1. In addition, inhibition of the generation of superoxide was measured with MitoSOX red probe (final concentration: 5 µM) as the same method.

TABLE 2

Results of anti-oxidant effect by using DHR 123

| Compound Number | $IC_{25}$ (µM) |
|---|---|
| Compound 9 | 0.10 |
| Compound 12 | 0.24 |
| Compound 13 | <0.1 |

EXPERIMENTAL EXAMPLE 1-3

Cell Protection Effect Against Oxidative Stress Induced by tBOOH

It is known that tertiary-butylhydroperoxide (tBOOH) induces cell necrosis by causing oxidative stress in various cells. Thus, inhibition of cell necrosis by anti-oxidant effect was measured by treating H9C2 cells with tBOOH. H9C2 cells were dispensed into each well of a 96-well plate ($1.5 \times 10^4$ cells/100 µl/well). The next day, the cells were pretreated with each compound and then treated with tBOOH (final concentration: 400 µM) for 2 hrs. 50 µl of formaldehyde was added to each well to fix the cells. Cells were fixed for 30 minutes and washed with distilled water three times. Then, the plate was completely dried in a 50° C. dry oven and SRB solution was added thereto to stain remaining protein. The plate was washed with 1% acetic acid and dried. Then, 100 µl of Tris solution (10 mM) was added to the plate to redissolve dye and $IC_{50}$ was calculated by measuring O.D. at 590 nm and 650 nm with a spectraMAX ELISA reader. Herein, the term "$IC_{50}$" refers to the concentration of compound which protects 50% of cells from necrosis induced by tBOOH treatment. The results are represented in the following Table 3.

TABLE 3

Cell protection effect against tBOOH

| Compound Number | $IC_{50}$ (µM) |
|---|---|
| Compound 2 | 6.5 |
| Compound 6 | 0.13 |

TABLE 3-continued

Cell protection effect against tBOOH

| Compound Number | $IC_{50}$ (µM) |
|---|---|
| Compound 9 | <0.2 |
| Compound 13 | <0.2 |
| Compound 14 | 0.72 |
| Example 1 | 0.6 |
| Example 2 | 2 |

EXPERIMENTAL EXAMPLE 1-4

Measurement of Removal Capacity of ONOO⁻ (peroxynitrite) by Using dihydrorhodamine 123

ONOO⁻ (peroxynitrite), which is known as a kind of RNS, plays a very important role in oxidative stress. Thus, it is very important to evaluate the removal capacity of ONOO⁻ of necrosis inhibitors. It is well known that DHR123 probe is oxidized by ONOO⁻. Thus, by using such a property, the capacity of each compound was measured.

10 µl of each compound, which was serially diluted 3-fold from 50 µM, was dispensed into each well of a 96-well plate, and then 170 µl of assay mixture (10 µM DHR123, 1×PBS, 100 µM DPTA without ONOO⁻) was added to each well. Finally, 20 µl of ONOO⁻ solution (final concentration: 1 µM) was added to initiate a reaction. Herein, the term "$IC_{50}$" refers to the concentration of compounds which causes 50% inhibition of oxidation of DHR123 by ONOO⁻.

The results for the structure-activity relationship (SAR) of ONOO⁻ removal capacity of compounds are represented in Table 4.

TABLE 4

ONOO⁻ removal capacity of compounds

| Compound Number | ONOO⁻ removal capacity ($IC_{50}$, µM) |
|---|---|
| Compound 5 | 3.4 |
| Compound 9 | 0.5 |
| Compound 12 | 0.21 |
| Compound 13 | 0.9 |

EXPERIMENTAL EXAMPLE 1-5

Direct Anti-Oxidant Effect on $H_2O_2$ and tBOOH

To know the anti-oxidant effects of necrosis inhibitors having indole structure, direct anti-oxidant effects on specific ROS, $H_2O_2$ (hydrogen peroxide) and tBOOH were evaluated.

10 µl of DHR123 probe (final concentration: 1.25 µM) was added to 10 µl of each compound which was diluted with 100 µl of DMEM complete media. $H_2O_2$ and tBOOH were added as the concentration shown in the following Table 5 and after 2 hrs, fluorescence at wavelengths (480 nm (ex)/538 nm (em)) was measured with spectraMax gemini. Herein, the term "$IC_{25}$" refers to the concentration of compound which causes 25% decrease of fluorescence assuming the amount emitted by oxidation of DHR123 caused by $H_2O_2$ or tBOOH was 100%.

TABLE 5

Direct anti-oxidant effect on $H_2O_2$ and tBOOH

| | $IC_{25}(\mu M)$ | | | |
|---|---|---|---|---|
| Compound No. | $H_2O_2$ (0.6 mM) | $H_2O_2$ (0.3 mM) | tBOOH (0.4 mM) | tBOOH (0.2 mM) |
| Compound 3 | 2.15 | 2.2 | 2.4 | 2 |
| Compound 4 | 3.6 | 2.3 | 5.8 | 3 |
| Compound 9 | 2 | 0.85 | 2.9 | 1.45 |
| Compound 12 | 2 | 1.65 | 3 | 1.95 |

EXPERIMENTAL EXAMPLE 2

Protective Effect of Compound 9 Against Liver Injury by Ischemia/Reperfusion In Beagle Dog Trial Design: 27 healthy beagle dogs (body weight: 8.5-11.5 kg) were selected for trial. The trial was conducted after permission was granted by the Asan Hospital Ethics Commission. To minimize the accumulation of glycogen in liver, the dogs had been fasting for 24 hours before the operation, and hair was removed. The dogs were divided randomly into the control group (n=9), Group B (n=6), Group C (n=6) and Group D (n=6). Endotracheal intubation was conducted, and the dogs were anesthesized with zoletil and 2.5% enflurane. Cefazolin and ketorolac were used respectively as an antibiotic and an analgesic according to the procedure approved by the commission.

Operation Procedure: The dogs were laid on the operating table with warm blankets and warm water bottles on either side. The left external jugular vein and right long saphenous vein were cannulated with 21 gauge IV catheter through an open approach. The right internal carotid artery was incised and cannulated so that the blood dynamics could be observed during the operation. After a complete intravenous approach was obtained, anesthesia was maintained by inhalation of 2.5% enflurane. Crystalloid solution was administered at the infusion rate of 15 mL/kg/hr.

Figure 19:
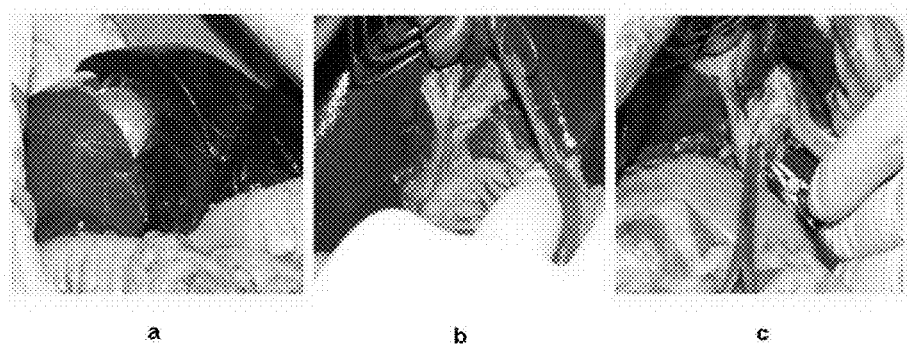
FIG. 19 is a photograph showing liver operation procedures in Experimental Example 2.

13 mg/kg, 4.5 mg/kg and 1.5 mg/kg of drug were respectively administered in Groups B, C, and D via IV 20 minutes before left hepatic inflow's were occluded. The concurrent dose and infusion were provided such that $C_{max}$ 12.5 mg/mL (at 20 min) was $C_{58}$ 5 mg/mL. During the operations, the blood pressure, heart rates, respiratory rate and arterial oxygen saturation were monitored every 15 minutes for all dogs. The operations were conducted by reverse T incision. Hepatoduodenal ligament was isolated after the lesser omentum was divided. The cholecyst and $4^{th}$ lobe of the liver were secured and the above structures were searched softly along with hilar structures. FIG. 19a shows the left and right lobes of the liver which were divided along Cantlie's line. FIG. 19b shows the traditional hilar structures. In humans, the right pedicle forms 60-70% of total liver volume. The hepatic inflow was occluded for 90 minutes to induce an ischemic injury, and the clamp was separated to induce a reperfusion injury for 60 minutes (FIG. 19c). Therefore, this model is a system using 90-minute ischemic injury and 60-minute reperfusion injury. After the operation, the abdominal cavity and skin were closed.

Figure 3:
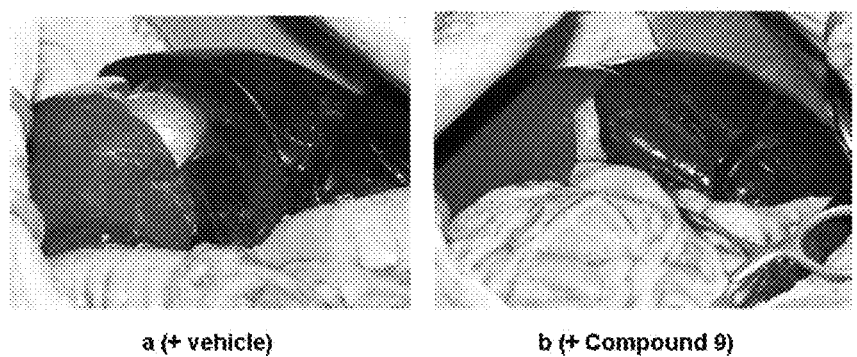
FIG. 3 is a photograph to compare the left hepatic lobe of Compound 9 treating group with that of the non-treating group.
Figure 4:
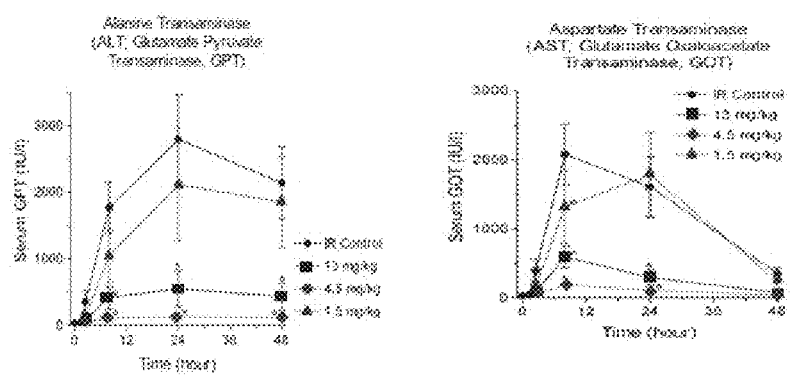
FIG. 4 is a graph representing ALT and AST values after ischemic reperfusion injury when Compound 9 is treated and not treated.
Figure 5:
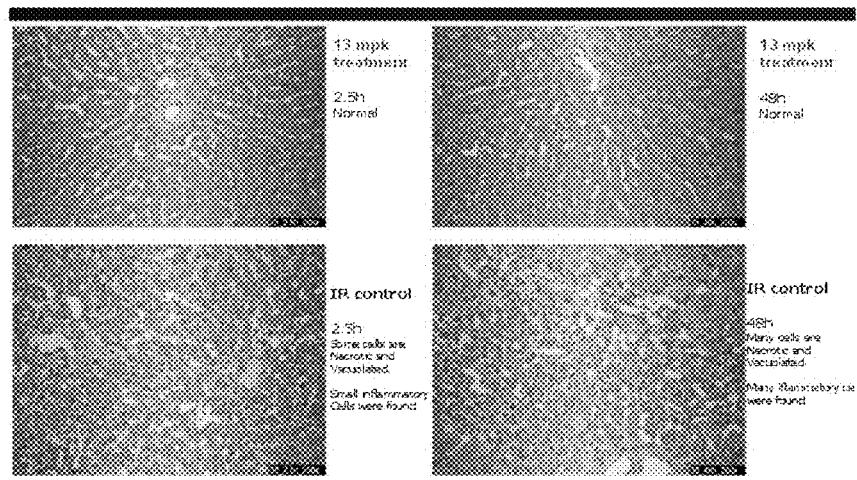
FIG. 5 is a photograph showing the comparison of tissue staining between the group in which 13 mg/kg of Compound 9 is administered and the group in which Compound 9 is not administered. (IR: ischemic reperfusion injury)

Blood sampling and biopsy: Blood sampling and biopsy were conducted at predetermined intervals including full blood counts (FBE; Hb, WCC, HCT, Plt, MCR, MCH and MCHC), liver function tests (LFT; AST, ALT, LDH and total bilirubin), urea and electrolyte (U&E; BUN and creatine), liver biopsy (histopathology and H&E staining) and HMGB1 measurement. A light micrograph and an electron micrograph were used to investigate the shape of the liver cells. The beagle dogs were kept in a warm and clean environment after the operation with administration of continuous analgesics and provision of a soft and high-protein diet. After 48 hours, they were sacrificed according to the procedure. The results are shown in FIGS. 3, 4 and 5.

Figure 6:
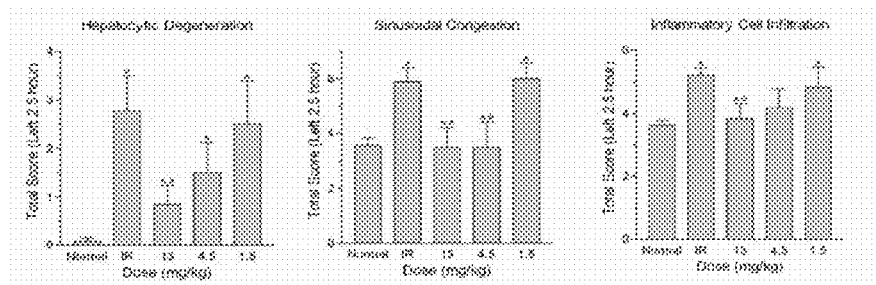
FIG. 6 is a graph showing the comparison results between Compound 9 treating groups and the non-treating group based on microscopic observation (hepatocytic degeneration, sinusoidal congestion and inflammatory cell infiltration).

Histological analysis after IR injury: Liver biopsy samples were fixed and dehydrated, and then embedded in paraffin. The paraffin blocks were cut 4 μm thick, stained by the Mayers hematoxylin-eosin method and investigated with a light microscope. Every sample was randomly distributed and analyzed by blind procedure. Hepatocytic cell degeneration and necrosis, sinusoidal and portal vein congestions, and inflammatory cell infiltration were investigated. According to the reported method (Hafez T et al., Journal of Surgical Research 2007; 138: 88-99), histological analysis results were graded quantitatively: (0 (0%, none), 1 (1-25%, mild), 2 (26-50%, moderate) or 3 (51-100%, marked). The results are shown in FIG. 6.

Figure 7:
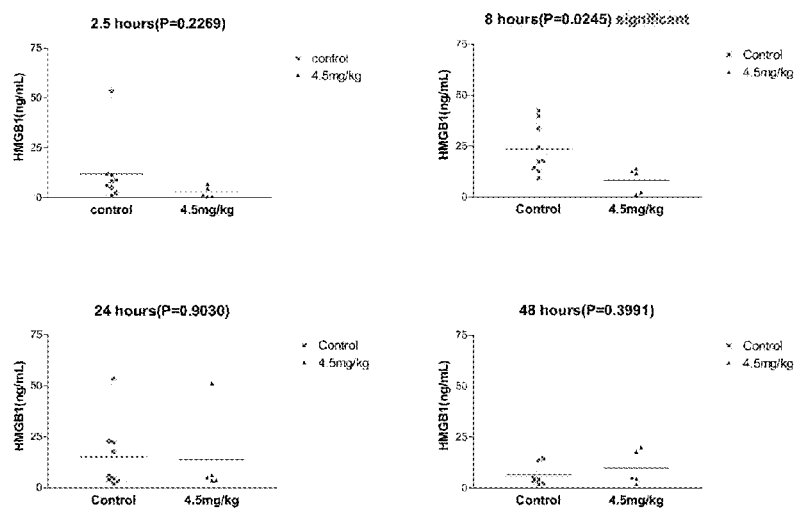
FIG. 7 is a graph showing the comparison of MGB1 level between the group in which 13 mg/kg of Compound 9 is administered and the ischemic reperfusion injury control group.

HMGB1 measurement: According to the manufactare's protocol using an HMGB1 ELISA assay kit, the HMGB1 were measured. The results are shown in FIG. 7.

Figure 8:
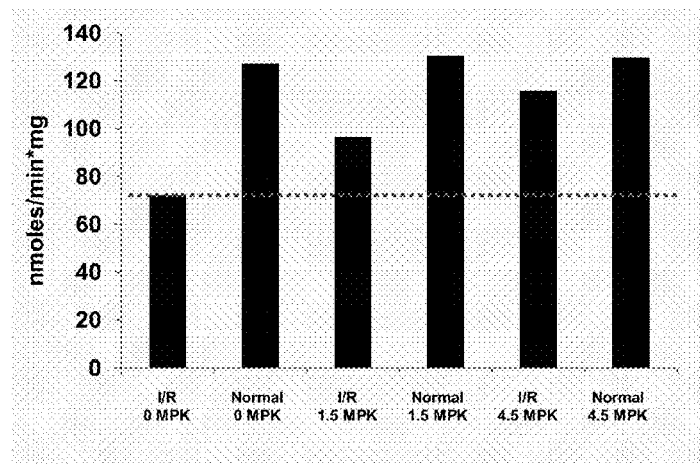
FIG. 8 is a graph showing the comparison of mitochondrial complex I activity after ischemic reperfusion injury between the Compound 9 treating group and the non-treating group.

Mitochondrial complex I activity measurement: Liver tissues were washed 2 times with ice-cold Buffer A (320 mm sucrose, 1 mM EDTA, 10 mM Tris (pH 7.5)). They were cut into small pieces and homogenized with 4 mL AT buffer (75 mM sucrose, 225 mM mannitol, 1 mM EGTA and 0.01% BSA, pH 7.4) per 1 g of pieces in a glass-teflon homogenizer. The homogenate was centrifuged at 4° C. for 5 minutes at 1000 g and the resulting supernatant was centrifuged two times at 13,000 g. A mitochondria-enriched mass was used for measurements of mitochondria complex I activity. Complex I activity (NADH: CoQ oxidoreductase) was measured by monitoring the rotenone-sensitive reduction of NADH in the presence of decylubiquinone at 340 nm. The results are shown in FIG. 8.

EXPERIMENTAL EXAMPLE 3

Preventive Effect on HMGB1 Release by Compound 9 After tBOOH treatment

It is well known that HMGB1 is released when cell necrosis happens. Thus, after the treatment of 400 μM tBOOH which causes oxidative stress, the preventive effect of Compound 9 on HMGB1 release was tested.

Figure 9:
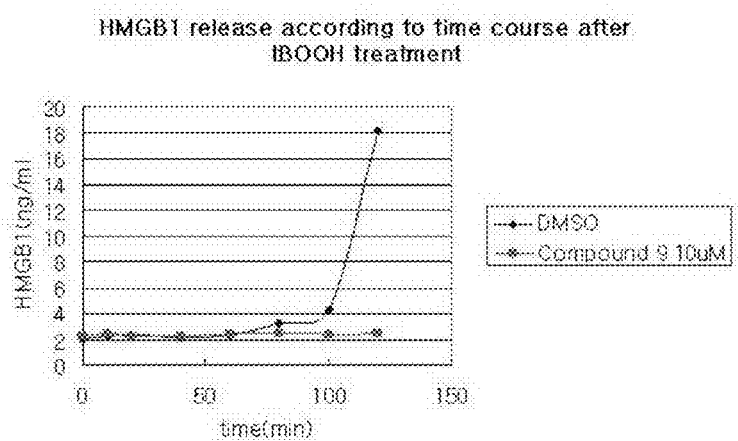
FIG. 9 is a graph representing HMGB1 release after treatment with Compound 9.

H9C2 cells were dispensed as $1.5 \times 10^4$ cells/100 μl/well. The next day, Compound 9 was treated at the concentration of 10 μM for 30 minutes. After treatment of tBOOH (final concentration: 400 μm), the level of HMGB1 was measured from 50 μl of supernatant with HMGB1 ELISA by the hour. The results are represented in FIG. 9.

EXPERIMENTAL EXAMPLE 4

Observation on the Change of Total ATP Content After tBOOH Treatment

Cells show a decrease of ATP content in the course of necrosis. The maintenance of ATP amount is very important to the survival of cells. Thus, after treatment with tBOOH, the change of ATP content was observed.

Figure 10:
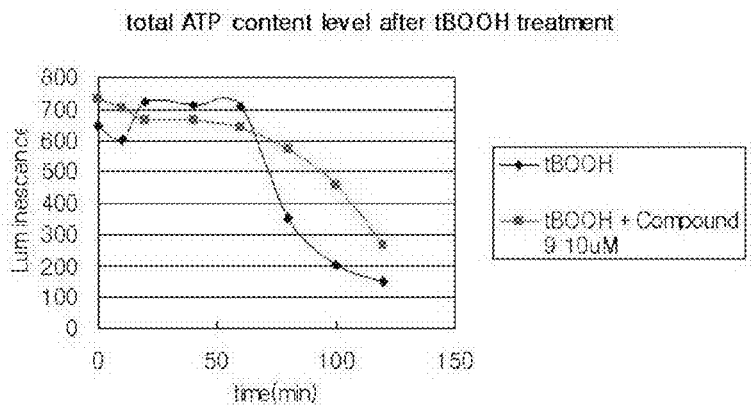
FIG. 10 is a graph representing the change of ATP content by Compound 9 after treatment with Compound 9.

H9C2 cells were dispensed as $1.5 \times 10^4$ cells/100 μl/well. The next day, Compound 9 was treated at the concentration of 10 μM for 30 minutes. After treatment with tBOOH (final concentration: 400 μM), the amount of ATP remaining in the cells was measured with an ATP monitoring kit (PerkinElmer Life Sciences). The results are represented in FIG. 10.

EXPERIMENTAL EXAMPLE 5

Protective Effect of Compound 9 on Cell Necrosis After In Vitro Ischemic Reperfusion Injury To measure the protective effect of Compound 9 on H9C2 cell necrosis after ischemic reperfusion injury, the following experiments were carried out: FDA and PI double staining, cell number counting, FACS assay and mitochondrial swelling measurement.

Cell culture and hypoxic injury condition: H9C2 cells were incubated in DMEM medium containing FBS and antibiotic. When 80-90% of cells were confluent, the experiment was carried out. 24 hrs prior to the experiment, H9C2 cells were inoculated into a 35 mm flask and a 150 mm flask. When about 80% of cells were confluent, medium was changed with DMEM medium containing 0.5% FBS and antibiotic. The cells were incubated in a hypoxic chamber for 24 hrs. At 23.5 hrs, in the hypoxic chamber the cells were treated with various chemicals (0.01% DMSO, Compound 9 (20 μM), vitamin C (10 μM) and z-VAD-fmk (20 μM)). The cells were transferred to a 37° C. incubator and then treated with $H_2O_2$ (400 μM) immediately before re-incubation. Reoxygenation was carried out for 1.5 hrs.

EXPERIMENTAL EXAMPLE 5-1

Measurement of Protective Effect Via FDA and PI Double Staining After Ischemic Reperfusion Injury in H9C2

Figure 11:
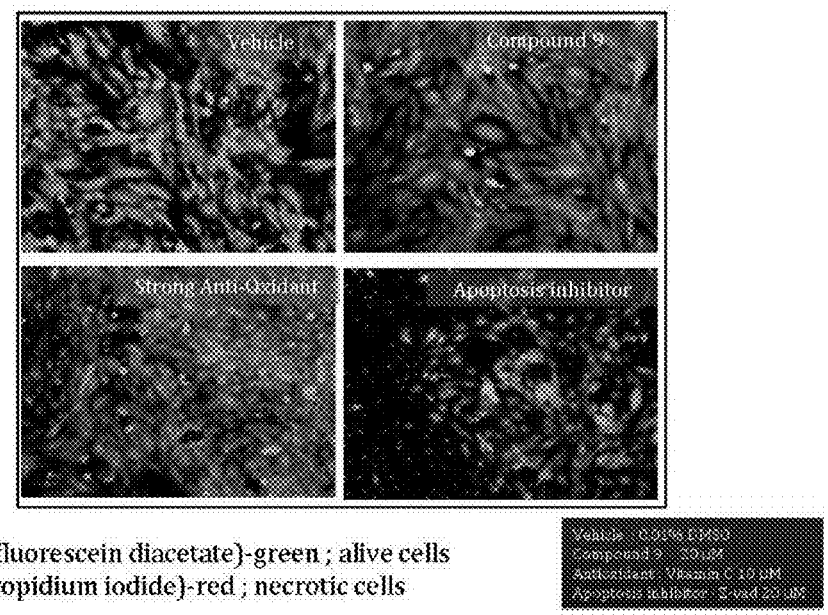
FIG. 11 is a fluorescence microscope photograph of H9C2 cells double stained with FDA and PI to show the protective effect of Compound 9 against necrotic cell death.

H9C2 cells incubated in a 35 mm flask for fluorescence were double stained with FDA (fluorescein diacetate, Sigma) and PI (propidium iodide). FDA and PI stock solutions were prepared. The cells were washed with PBS, and 4.5 μl of FDA solution (5 mg/ml) and 4 μl of PI solution (2 mg/ml) were added to 1.5 ml of cell culture medium. Images stained with FDA/PI were obtained by a fluorescence microscope. The results are shown in FIG. 11.

EXPERIMENTAL EXAMPLE 5-2

Measurement of Protective Effect by Counting Cells Double Stained with FDA and PI After Ischemic Reperfusion Injury in H9C2

Figure 12:
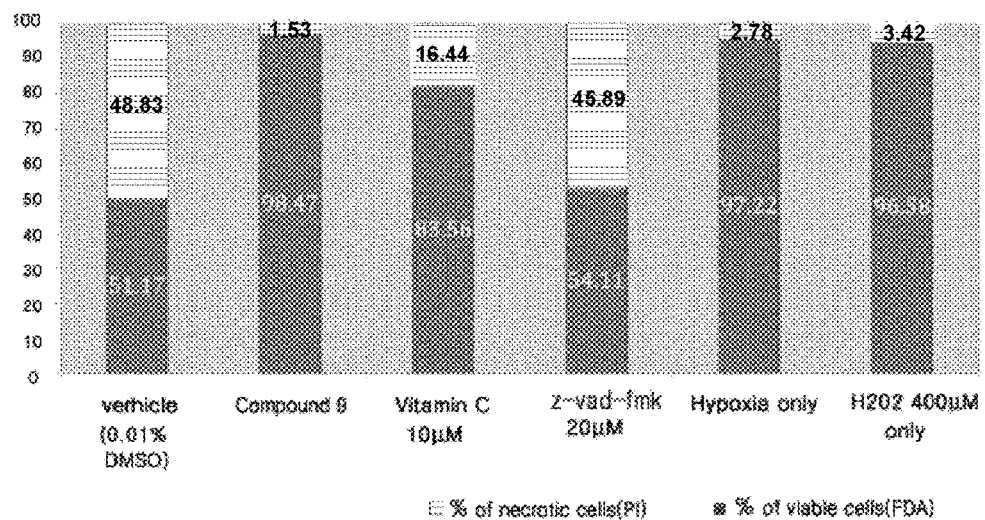
FIG. 12 is a graph representing direct cell counting to show the protective effect of Compound 9 against necrotic cell death.

After obtaining an FDA/PI stained image by a fluorescence microscope in Experimental Example 5-1, the number of live cells and dead cells was counted by rising Image Pro. The results are represented in FIG. 12.

EXPERIMENTAL EXAMPLE 5-3

Measurement of Protective Effect by FACS Analysis of Cells Double Stained with Annexin V and PI After Ischemic Reperfusion Injury In H9C2

Figure 13:
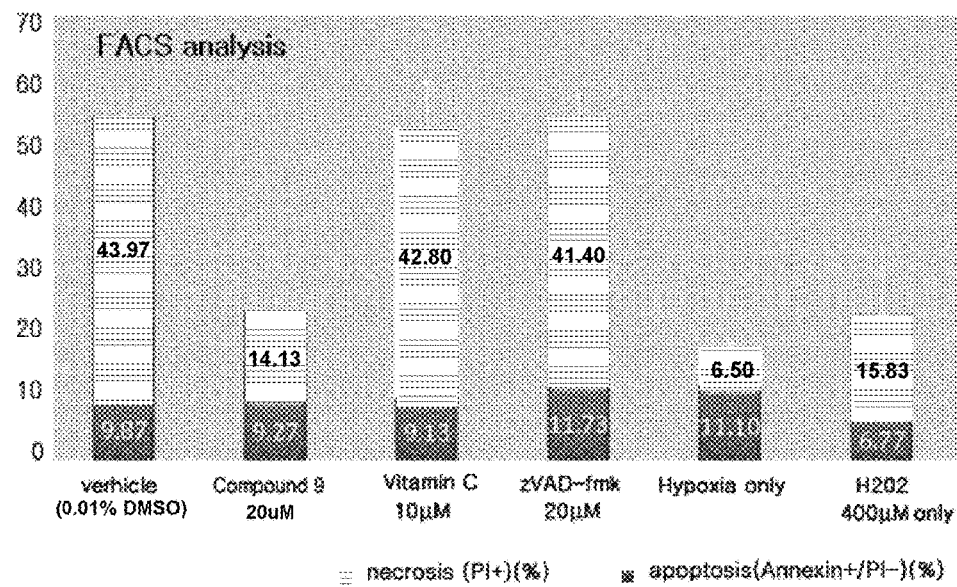
FIG. 13 is a graph representing FACS analysis results to show the protective effect of Compound 9 against necrotic cell death.

Apoptotic or necrotic cells were stained with FITC and Annexin V apoptosis detection kit, and then analyzed by using a flow cytometer. Cells incubated in a 35 mm flask were divided into three (3) groups according to staining with PI and Annexin V-FITC: non-treatment single staining and double staining. After reoxygenation, the collected cells were centrifuged at 2,000 rpm at 4° C. for 10 minutes. After removal of supernatant medium, the cells were resuspended with Annexin V-binding buffer, stained with 5 μl of PI and 5 μl of Annexin V-FITC for 15 minutes in dark, and then analyzed via FACS. The results are shown in FIG. 13.

EXPERIMENTAL EXAMPLE 5-4

Measurement of Inhibitory Effect on Mitochondria Swelling After Ischemic Reperfusion Injury in H9C2

Figure 14:
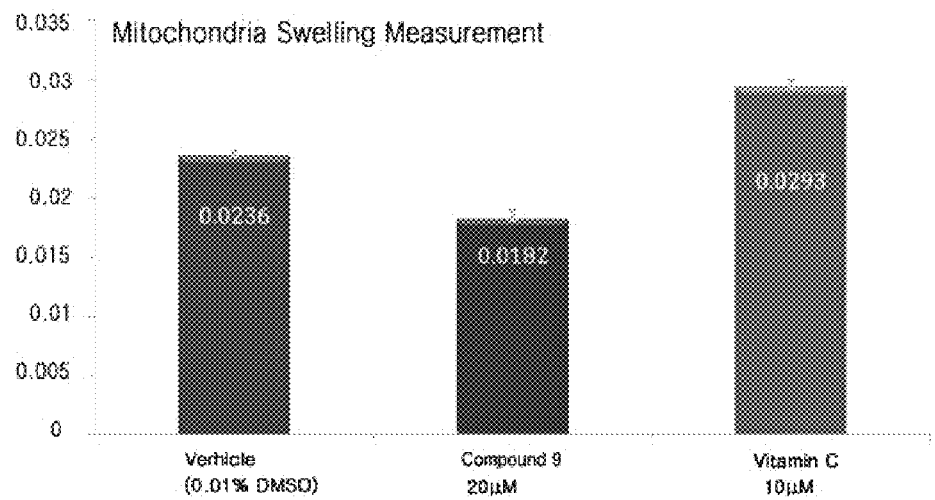
FIG. 14 is a graph showing the inhibitory effect of Compound 9 on mitochondrial swelling.

H9C2 cells incubated in a 150 mm flask were used for measuring mitochondria swelling. The cells were collected with 0.05% trypsin and then centrifuged at 2,000 rpm at 4° C. for 10 minutes. After removal of supernatant, the cells were washed with PBS. The cells were re-centrifuged at 2,000 rpm at 4° C. for 10 minutes, and then supernatant was discarded. The obtained cell mass was added to 500 μl of filtrated isolating buffer (300 mM Mannitol, 0.2 mM EDTA, 5 mM Tris-HCI (pH 7.4), 1% bovine serum albumin) and used fix subsequent experiments. Cells broken with a syringe were tested with a trypan blue stain solution. When most of the cells were broken, cell solution was immediately centrifuged at 2,000 rpm for 4 minutes. Supernatant containing mitochondria was collected and centrifuged at 13,000 rpm at 4° C. for 10 minutes. After supernatant was discarded, the obtained mitochondria mass was resuspended in 100 μl of incubation buffer (150 mM KCI, 20 mM Tris-HCI (pH 7.4)). The protein concentration was measured with a protein quantification kit. Some of isolated mitochondrial proteins were dispensed into a 96-well plate and then measured with a spectrophotometer at 513 nm. The results are represented in FIG. 14.

EXPERIMENTAL EXAMPLE 5-5

Measurement of Mitochondrial Turbidity and Nucleus Necrosis by Using MitoTracker and PI Double Staining After Ischemic Reperfusion Injury In H9C2

Mitochondrial visualization and 3D image: To visualize the mitochondria of H9C2 cells incubated in a 35 mm flask, 1 mM MitoTracker Green FM dissolved in DMSO was prepared. The cells were washed with cell culture medium and then double stained with 0.5 mM MitoTracker Green FM and 4 μl of PI solution. After 1 hr, the cells were analyzed by a fluorescence microscope, and a 3D image was obtained by using the Imaris program.

Electron microscope: H9C2 cells, which were incubated in a 24-well plate having coverslip on the bottom, were used. The cells were fixed with 0.1 M sodium phosphate buffer (pH 7.4) containing 2% glutaraldehyde. The cells were washed with PBS buffer and then postfixed with 1% $OsO_4$ and 1.5% potassium for 1 hr. The cells were sequentially washed with PBS buffer and distilled water twice, and then treated with filtrated 0.5% uranyl acetate at 4° C. overnight. The cells were washed with distilled water twice, dehydrated with ethanol and embedded in Epon twice, for 1 hr at a time. The cells were polymerized in Epon at 60° C. for 2 days and then analyzed via electron microscopy.

Figure 15:
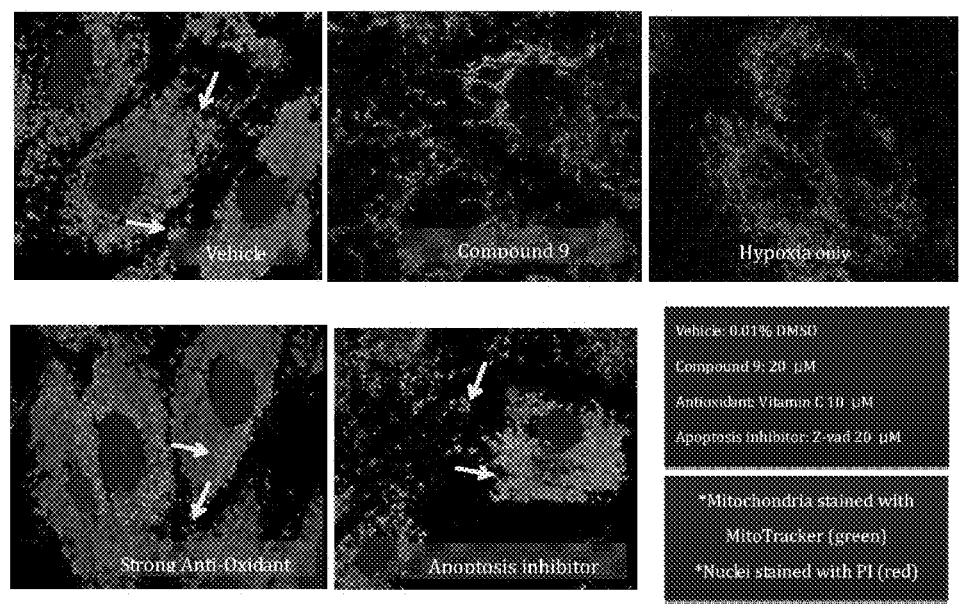
FIG. 15 is a fluorescence microscope photograph showing the mitochondrial protective effect of Compound 9.

Fluorescence immunostaining: OCT-embedded tissue slices were washed with ice-cold 0.05% TBST for 10 minutes three times. Tissue slices were treated with a blocking solution containing 1% BSA at room temperature for 1 hr. To carry out immunofluorescence staining for heavy chain cardiac myosin, tissue slices were treated with anti-heavy chain cardiac myosin (1:100, Abcam) as a primary antibody. Tissue slices were washed with PBS-Tween 20 twice and then stained with a secondary antibody, donkey anti-mouse 633 IgM (Invitrogen) and washed with PBS-Tween 20 twice. For wheat germ agglutinin staining, tissue slices were treated with Alexa Fluor 555 wheat germ agglutinin (Invitrogen) at 37° C. 10 minutes. To carry out immunofluorescence staining for alpha-sarcomeric actin, tissue slices were treated with a primary antibody, anti-alpha-sarcomeric actin, at 4° C. for 24 hrs. Tissue slices were washed with 0.05% TBST twice and then stained with a secondary antibody, Alexa Fluor 555 donkey anti-mouse IgG (Invitrogen). Tissue slices were stained with hematoxylin for 5 seconds to stain the nucleus. After mounting of tissue slices, images were obtained from a fluorescence microscope. The results are shown in FIG. 15.

EXPERIMENTAL EXAMPLE 6

Protective Effect of Compound 9 Against Heart Injury By Ischemia/Reperfusion In SD Rats Animal management: Male SD rats (270-360 g) were purchased from Seoul National University Animal Center. The rats were kept in the semi-specific pathogen-free condition in which the light was turned on and off on a 12-hour cycle, the temperature and humidity were maintained at 22° C. and 55%, respectively. Standard solid rodent chow and tap water ad libitum were provided. Every animal had an adaptation period of 1 week before the experiment, which proceeded with the permission of IACUC at Seoul National University.

Operation preparation: After an adaptation period of 1 week, the rats here anesthetized with a mixture of ketamine (100 mg/kg, Yuhan Corp., Seoul, Korea), and xylazine (10 mg/kg, Bayer, Shawnee Mission, Kans., USA) via intraperitoneal infusion. After appropriate anesthesia, basic echocardiographic evaluation was conducted and then 100% of oxygen was provided for all rats.

The ischemic reperfusion was induced by temporary ligation of LAD for 45 minutes. LAD was ligated with 8-0 Ethilon (Ethicon) with polyethylene 10 tubing for 45 minutes. Ischemia was identified with the naked eye by the decoloration of myocardium and ventricular tachyarrhythmia.

The rats were divided into three groups: control group (5 mL of 0.9% saline), cyclosporine—treated group (25 mg/kg in 5 mL of 0.9% saline), and Compound 9—treated group (30 mg/kg in 5 mL of 5% dextrose). The drugs were infused for 20 minutes via a tail vein using an animal infusion pump.

The reperfusion was started by removing the ligation and polyethylene 10 tubing, and characteristics due to typical hyperemic change of injured myocardium during the first several minutes were defined as reperfusion. The loose suture pieces were retained to define the ischemic area for termination.

After operation, Compound 9 was orally administered once a day at the same dose for 3 days to the Compound 9—treated group. The remaining groups were administered at the same dose.

The function investigation of infarcted rat heart by echocardiography: At the state of anesthesia, the hair of the left hemithorax was removed. A transthoracic echocardiography was conducted immediately before a coronary ligation, and data were collected using a Doppler echocardiographic system with a linear-array transducer. The heart was imaged with a 2-dimensional mode of parasternal long-axis and short-axis view. A short-axis view including a papillary muscle was used to position the M-mode cursor vertically with the interventricular septum and LV posterior wall. The images obtained during the training period were not recorded. The left ventricular end-diastolic (LVEDD) and end-systolic dimensions (LVESD) were measured according to the method of leading-edge technology of American Society of Echocardiography. The percent (%) of fractional shortening of LV was calculated by the equation of 100× (LVEDD-LVESD)/LVEDD.

Tissue analysis of infarcted rat heart: 3 days after the event of myocardial ischemia, the rats were anesthesized. To evaluate the size of the infraction, the paraffin-embedded representative LV slices were cut into 4 μm thick slices. Neutrophils were stained with hematoxylin and eosin, and then investigated with a light microscope. The numbers of inflammatory cells were measured in the area of 1 $mm^2$ of each slice. The fibrosis area stained with Masson's trichrome was investigated using an image-analysis system (Image Pro version 4.5; MediaCybernetics, Bethesda, Md., USA) The measurement of the fibrosis area was conducted for 2 individual slices and the mean value was used for numerical analysis.

For immunohistological staining, and investigation, rat beans were put into an OCT-compound having 8 μm slices (Tissue-Teck, Sakura, Torrance, Calif., USA), frozen rapidly and stored. The staining was quantitatively measured by the number of positive cells for staining in 10 HPF per animal (n=3). To evaluate apoptosis, TUNEL assay (Chemicon S7100 kit, Chemicon, Temecula, Calif., USA) and immunohistological staining for caspase-3 were conducted. The positive cells for TUNEL assay or caspase-3 were investigated in 10 different microscope areas for at least 3 different slices per animal.

Immunofluorescence staining was conducted using an anti-cardiac troponin I (Santa Cruz Biotechnology). Green FITC conjugated goat anti-rabbit IgG antibody (Molecular Probes) was used for detection. Red PI staining was conducted to represent nucleus, and blue Atom HMGB1 staining by Fluro 350 was conducted to represent nucleus. The colocalization of red Dil-labeled MSC and green connexin-43 or cardiac troponin I expression was investigated with a fluorescece microscope (LSM 510 META, Carl Zeiss, Peabody, Mass., USA).

Infarct Size Measurement: Infarct size was determined 72 hours after I/R injury of myocardium was evaluated with AAR (area at risk) percent. The ratio of AAR to LV (left ventricle) represents the degree of myocardium tissue affected with I/R. The ratio of IS/AAR is an accurate index for determining IS in the injured myocardium and it is the primary end point to evaluate the efficacy of drug treatment. To determine AAR, the left coronary artery was ligated again, and 4% Evans Blue dye was infused via thoracic aorta by retrograde method. The heart was removed quickly, washed in 0.9% saline and then stored in a freezer (−20° C.). The heart was cut into five 1 mm cross slices. The heart slices were stored in 1% triphenyltetrazolium chloride solution for 15 min at 37° C. and then put into formaldehyde solution. The normal tissue was dyed red, and the infarcted tissue was dyed white. Pictures were taken of the heart slices in digital mode (Canon EOS 400D) under a microscope, and IS, AAR, and the total LV area were measured using ImagePro software (version 1.34).

Numerical analysis: All data were represented by a mean value (SE). The consecutive variables are compared by Student-t test, and multiple comparisons were conducted by variance analysis with Bonferroni post hoc correction. If p-value is less than 0.05, the value was considered statistically significant, and all analysis was conducted using SPSS version 17.0 (SPSS Chicago, Ill., USA).

Figure 16:
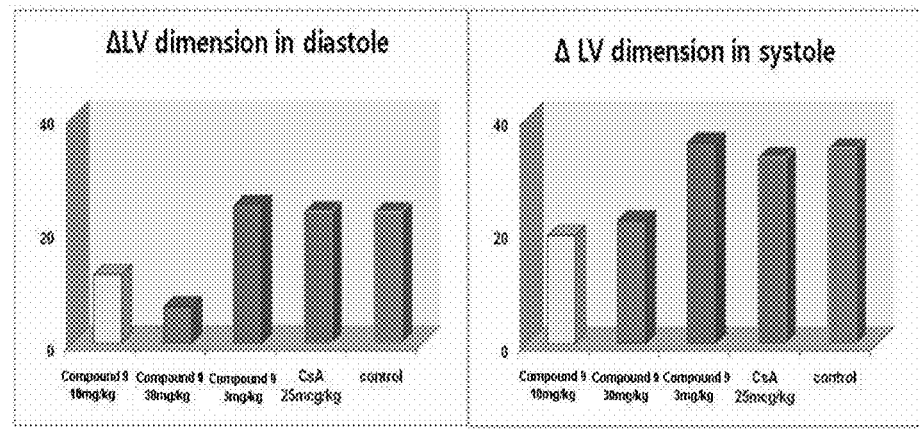
FIG. 16 is a graph showing the inhibitory effect of Compound 9 on left ventricle swelling in the ischemic reperfusion injury model.
Figure 17:
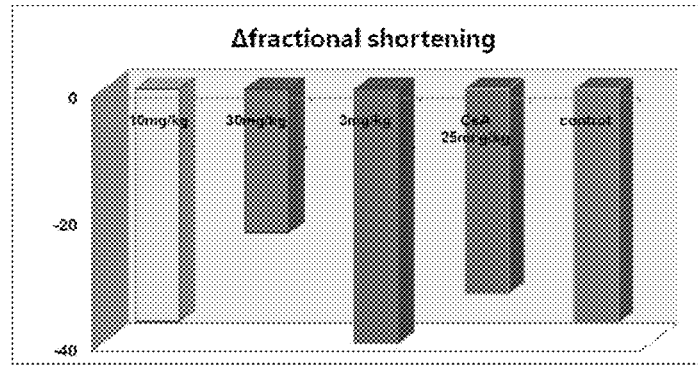
FIG. 17 is a graph showing the inhibitory effect of Compound 9 on left ventricular fractional shortening after ischemic reperfusion injury.
Figure 18:
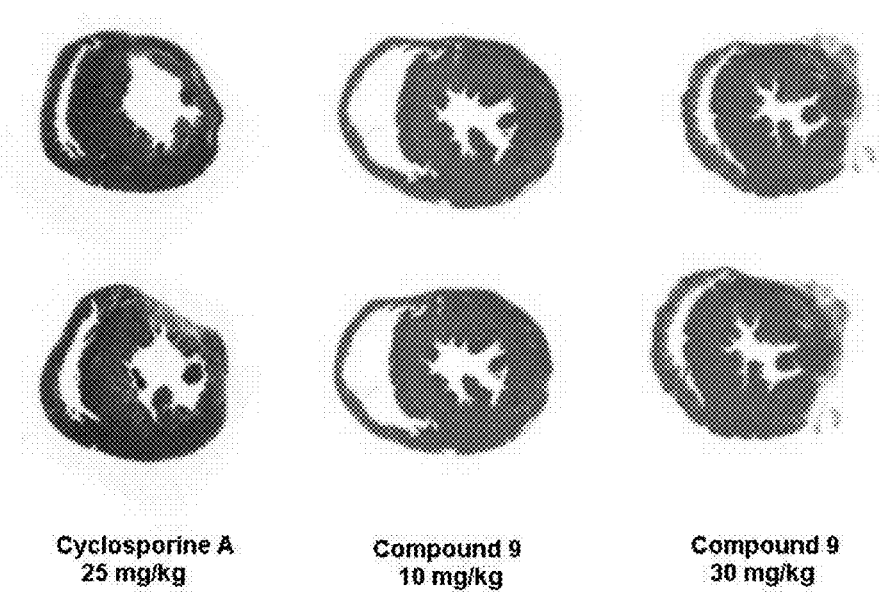
FIG. 18 is an image showing heart fibrosis by the MT (Masson-Trichrome) staining method to compare Compound 9 with Cyclosporine A.

The suppression effect of Compound 9 against increasing the left ventricular mass (LV) is shown in FIG. 16, and the suppression effect of Compound 9 against LV fractional shortening after I/R injury is shown in FIG. 17, and the comparison analysis result for Compound 9 with CsA for myocardial fibrosis is shown in FIG. 18.

The invention claimed is:

1. A method for the treatment of diseases associated with oxidative stress which is mediated by reactive oxygen species (ROS) or reactive nitrogen species (RNS) selected from the group consisting of cardioplegia and myocardial infarction, comprising
administering a composition which comprises a therapeutically-effective amount of (tetrahydropyran-4-yl)-[2-phenyl-5-(1,1-dioxo-thiomorpholin-4-yl)methyl-1H-indol-7-yl]-amine, or pharmaceutically acceptable salt or isomer thereof as an active ingredient; and a pharmaceutically acceptable carrier to a subject in need thereof.

2. The method of claim 1, wherein the diseases associated with oxidative stress is myocardial infarction.

* * * * *